United States Patent [19]

Crooks et al.

[11] Patent Number: 5,776,957
[45] Date of Patent: Jul. 7, 1998

[54] NORNICOTINE ENANTIOMERS FOR USE AS A TREATMENT FOR DOPAMINE RELATED CONDITIONS AND DISEASE STATES

[75] Inventors: Peter A. Crooks; Linda Phyliss Dwoskin; Michael Thomas Bardo. all of Lexington, Ky.

[73] Assignee: The University of Kentucky Research Foundation. Lexington, Ky.

[21] Appl. No.: 749,404

[22] Filed: Nov. 15, 1996

[51] Int. Cl.$^6$ ................................................ A61K 31/44
[52] U.S. Cl. ................................................ 514/343
[58] Field of Search ................................................ 514/343

[56] References Cited

U.S. PATENT DOCUMENTS

| | | | |
|---|---|---|---|
| 4,321,387 | 3/1982 | Chavdarian et al. | 546/276.4 |
| 4,442,292 | 4/1984 | Edwards, III | 546/278.4 |
| 4,965,074 | 10/1990 | Lesson | 424/449 |
| 4,966,916 | 10/1990 | Abood | 514/534 |
| 5,138,062 | 8/1992 | Osdene et al. | 546/329 |
| 5,214,060 | 5/1993 | Caldwell et al. | 514/343 |
| 5,223,497 | 6/1993 | Gawin et al. | 514/225.2 |
| 5,227,391 | 7/1993 | Caldwell et al. | 514/343 |
| 5,232,933 | 8/1993 | Lippiello et al. | 514/343 |
| 5,242,934 | 9/1993 | Lippiello et al. | 514/343 |
| 5,276,043 | 1/1994 | Lippiello et al. | 514/343 |
| 5,278,045 | 1/1994 | Tam | 435/7.8 |
| 5,278,176 | 1/1994 | Lin | 514/343 |
| 5,594,011 | 1/1997 | McDonald et al. | 514/343 |

FOREIGN PATENT DOCUMENTS

WO94/24848  11/1994  WIPO.

OTHER PUBLICATIONS

"The Pharmacological Basis of Therapeutics". Fourth Edition. A. Goodman et al, 1970.

"The Pharmacological Basis of Therapeutics". Eighth Edition. Gilman et al, 1990.

Molecular Pharmacology. E.C. Hume et al, vol. 14, pp. 737–750, 1990.

Pharmocological Biochemical Behavior, Wegner et al, vol. 46:435–443, 1993.

"Principles of Drug Action". Second Edition. Goldstein et al, 1974.

Chemical Abstracts 122:233216, "Minor Alkaloids of Tabacco Release [3H]Dopamine From Superfused Rat Striatal Slices", Dwoskin et al, 1995.

Chemical Abstracts 119:108808, "S(-)-Nornicotine Increases Dopamine Release in a Calcium-Dependent Manner From Superfused Rat Striatal Slices", Dwoskin et al, 1993.

Ricky Yeargan et al., "Tissue partitioning of cadmium in transgenic tobacco seedlings and field grown plants expressing the mouse metallothionein 1 gene", Transgenic Research 1, 261–267 (1992).

Indu B. Maiti et al., "Properties of transgenic plants that express a functional potyvirus P1 proteinase gene", 1995, pp. 1–18.

Indu B. Maiti et al., "Properties of transgenic plants that express a functional potyvirus p1 proteinase gene or a fused CP gene", 8th International Congress Molecular Plant–Microbe Interactions, Jul. 14–19, 1996 (Abstract #B–78).

Indu B. Maiti et al., "Expression of the Tobacco vein mottling virus nuclear inclusion protein (Na) gene in tobacco". J. Cell. Biochem. Supplement 16F, (Abstract #Y213).

Indu B. Maiti et al., "Seed–Transmissable Expression of Mammalian Metallothionein in Transgenic Tobacco", Biochemical and Biophysical Research Communications, vol. 150, No. 2, 1988, pp. 640–647.

Indu B. Maiti et al., "Expression of the Tobacco Vein Mottling Virus Coat Protein (CP) and Cylindrical Inclusion Proteion (C1) Genes in Tobacco", 3rd International Congress Int. Soc. Plant Mol. Biol. meeting Oct. 6–11, 1991 (Abstract #1154).

Indu B. Maiti et al., "Plants that Express a Potyvirus Proteinase Gene are Resistant to Virus Infection", Proc. Natl. Acad. Sci., vol. 90, pp. 6110–6114 (1993).

Indu B. Maiti et al., "Light Inducible and Tissue–Specific Expression of a Chimeric Mouse Metallothionein cDNA Gene in Tobacco", Plant Science, 76 (1991) pp. 99–107.

Indu B. Maiti et al., "Inheritance and Expression of the Mouse Metallothionein Gene in Tobacco", Plant Physiol. (1989) 91, pp. 1020–1024.

Indu B. Maiti et al., "Developing Genetically Engineered Disease, Pest and Herbicide Resistance in Tobacco", Recent Advances in Tobacco Science, vol. 18, Sep. 27–30, 1992, pp. 45–68.

Franklin et al., "Genetic Transformation of Peanut and Bean Callus Via Agrobacterium–Mediated DNA Transfer", Jour. of Cell. Bio. Abstract Y141, Apr. 3–16, 1992, p. 214.

Indu B. Maiti et al., "Multiple Potyvirus Genes do not Confer Protection Upon Plants Additively", 4th Congress of ISPMB meeting, Jun. 19–24, 1994 (Abstract #1533).

Indu B. Maiti et al., "Promoter/leader deletion analysis and plant expression vectors with the figwort mosaic virus (FMV) full length transcript (FLt) promoter containing single or double enhances domains", Transgenic Research 5.

G. Jason Smith et al., "Expression of Heterologous Genes Following Electroporation of the Marine Diatom Skeletonema Costatum", Plant Physiology, Abstract 803, Jun. 1995, vol. 108, No. 2.

Bird et al., "Transgenic Plants With Increased Solids Content", Chemical Abstracts, vol. 119, Abstract No. 19725In, 1993, p. 260.

Franklin et al., "High Expression of a Foreign Gene in Transformed Bean Callus", In Vitro Cellular & Development Biology, Mar. 19, 1992, vol. 28, No. 2, Abstract P–1119.

Rie Terada et al., "Expression of CaMV35S–GUS gene in transgenic rice plants", Molecular & General Genetics, vol. 220, pp. 389–392, 1990.

*Primary Examiner*—Frederick Krass
*Attorney, Agent, or Firm*—McDermott, Will & Emery

[57] ABSTRACT

Optically active nornicotine compounds as a treatment for dopamine-related conditions and disease states. Such disease states include the treatment of myasthenia gravis, Parkinson's disease, Alzheimer's disease, schizophrenia, eating disorders, ulcers, drug addiction and as a substitute for psycho-stimulant self-administration.

16 Claims, 20 Drawing Sheets

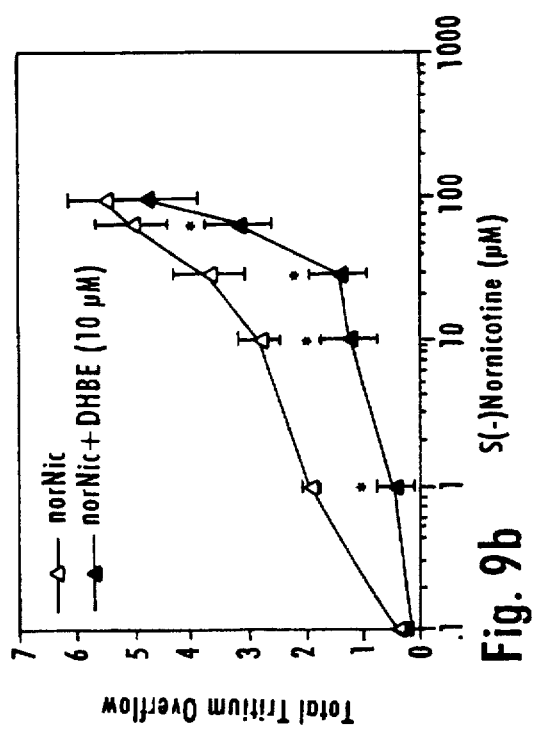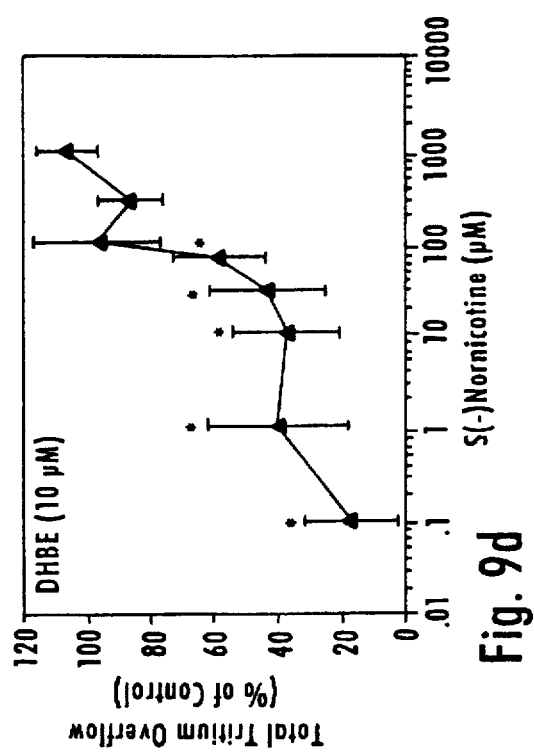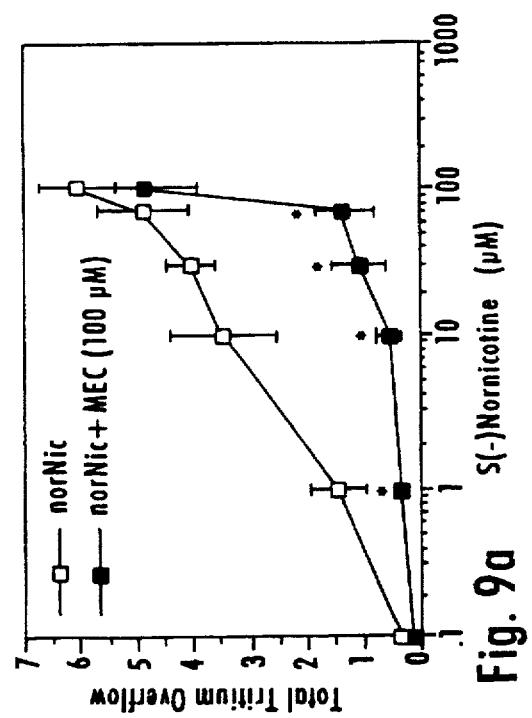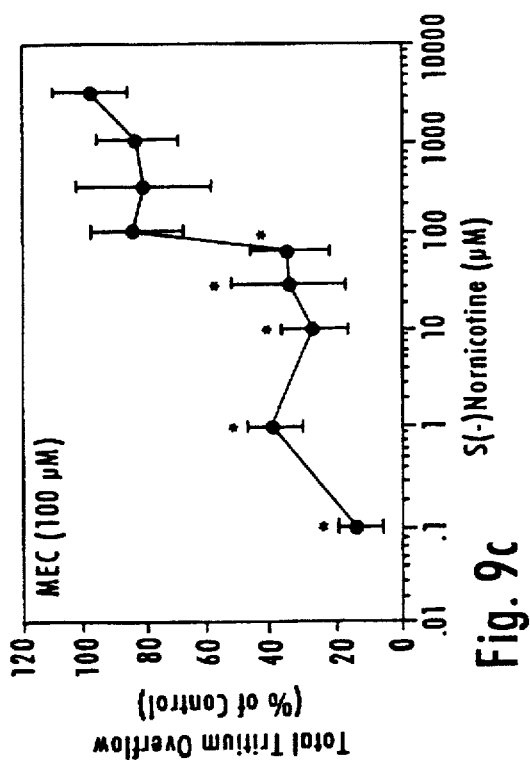

NORNICOTINE ENANTIOMERS FOR USE AS A TREATMENT FOR DOPAMINE RELATED CONDITIONS AND DISEASE STATES

TECHNICAL FIELD

This invention is directed to the use of optically active nornicotine compounds as a treatment for dopamine-related conditions and disease states. Such disease states include the treatment of myasthenia gravis, Parkinson's disease, Alzheimer's disease, shizophrenia, eating disorders, drug addiction and use of nornicotine enantiomers as a substitute for psycho-stimulant self-administration.

The compounds of the present invention have the formula as follows:

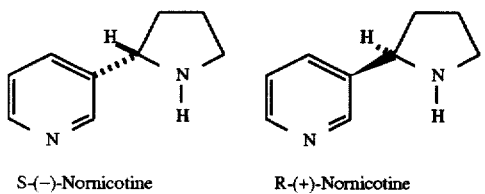

S-(−)-Nornicotine    R-(+)-Nornicotine

BACKGROUND ART

Many disease states and conditions are associated with nicotinic receptors and dopamine release. These include myasthenia gravis, Parkinson's disease, Alzheimer's disease, shizophrenia, eating disorders and drug addiction to name a few.

The behavioral effects of nicotine are attributed to an action on the CNS, since most of the effects are blocked by mecamylamine (Clarke, 1987) and more recently by dihydro-β-erythroidine (DHβE; Damaj et al., 1995). Mecamylamine is a CNS-active, noncompetitive nicotinic antagonist (Loiacono et al., 1993; Peng et al., 1994), and DHβE is a selective, competitive nicotinic receptor antagonist (Alkondon and Albuquerque, 1991; Mulle et al., 1991). Mecamylamine blocks nicotine interoceptive cues in discrimination studies (Stolerman et al., 1984), and mecamylamine pretreatment has been shown to influence cigarette smoking behavior and the subjective effects of nicotine (Stolerman et al., 1973; Rose et al., 1994).

Pharmacokinetic studies have quantitated NIC in brain after various routes of administration in several animal species (Nordberg et al., 1989, Plowchalk et al., 1992; Saji et al., 1992). However these studies did not determine the relative concentrations of NIC and its metabolites in brain. In a few studies, fractional analysis of NIC and its metabolites in brain were performed. [$^{14}$C]COT and [$^{14}$C]NIC-N-oxide were detected by high pressure liquid radiochromatography (ID: LRC) in mouse brain following i.p. administration of [$^{14}$C-N-methyl]NIC (Stalhandske, 1970, Petersen et al., 1984). N-Demethylated metabolites of NIC (e.g., norNIC and norCOT) were not detected in these studies, since the radio label is lost during NIC metabolism. Surprisingly, COT was not found in rat brain after peripheral NIC injection when analyzed by gas liquid chromatography-mass spectrometry and single ion monitoring (Deutsch et al., 1992). Investigators have found NIC metabolites to be pharmacologically active (Risner et al., 1985, 1988; Goldberg et al., 1989, and, Dwoskin et al., 1993, 1996; Teng et al., 1996).

As set forth below, various nicotine compounds and their uses are known. For example, U.S. Pat. No. 4,965,074 to Leeson discloses a nicotine derivative compound for the treatment of senile dementia and Alzheimer's type diseases. The patent does not disclose the use of an isolated enantiomer of nornicotine.

U.S. Pat. No. 5,278,176 to Lin is directed to nicotinic agonists. These compounds are useful for attentional hyperactivity disorder, and anxiety associated cognitive impairment or substance abuse withdrawal. The patent does not disclose the use of an isolated enantiomer of nornicotine.

U.S. Pat. No. 5,276,043 to Lippiello et al. is directed to nicotine derivatives useful for the treatment of neurodegenerative diseases. The patent does not disclose the use of an isolated enantiomer of nornicotine.

U.S. Pat. No. 5,227,391 to Caldwell et al. is directed to an R-(+) nicotine compound. The patent does not disclose the use of an isolated enantiomer of nornicotine. U.S. Pat. No. 5,214,060 to Caldwell et al. discloses compounds for the treatment of neurodegenerative diseases.

U.S. Pat. No. 5,242,934 to Lippiello et al. is directed to gamma nicotine compounds for the treatment of neurodegenerative diseases. U.S. Pat. No. 5,223,497 to Gawin et al. is directed to compounds for treating habit disorders. U.S. Pat. No. 5,278,045 to Tam discloses nicotine compounds for the enhancement of dopaminergic function.

U.S. Pat. No. 5,232,933 to Lippiello et al. discloses α-nicotine compounds for the treatment of neurodegenerative diseases. U.S. Pat. No. 5,138,062 to Osdene et al. discloses nicotine compounds. U.S. Pat. No. 4,966,916 to Abood discloses agonists and antagonists to nicotine as smoking deterrents. The patent discloses testing with enantiomers of nicotine in column 6 and also testing with n-ethyl nornicotine.

U.S. Pat. No. 4,442,292 to Edwards, III discloses nicotine analogs for use as insecticides. U.S. Pat. No. 4,321,387 to Chavdarian et al. discloses compounds of the formula which are nicotinoids of chiral nature for use as insecticides.

Merck Index, 11th Ed. 1989, Merck and Co., Inc., Abstract No. 6631 discloses the compound nornicotine is known. The abstract indicates that the compound is known to be useful as a horticultural insecticide.

Dwoskin et al., J. of Neurochemistry, volume 60, No. 6, 1993, published June, 1993. The article is entitled " S(−) Nornicotine Increases Dopamine Release in a Calcium Dependent Manner from Superfused Rat Striatal Slices. The publication does not compare R-(+) and S-(−) nornicotine isomers directly on dopamine function. The publication does not disclose the use of these compounds for the treatment of disease states including myasthenia gravis, Parkinson's disease, Alzheimer's disease, and smoking withdrawal.

The Journal of Psychopharmacology, June 1994, Vol. 115 (1–2) p. 31–36 discloses "PET studies of the uptake of (S) and (R) [11C] nicotine in the human brain: difficulties in visualizing specific receptor binding in vivo.

There is a need in the art for alternative treatments for dopamine-related conditions and disease states. Such disease states include, but are not limited to the treatment of myasthenia gravis, Parkinson's disease, Alzheimer's disease, schizophrenia, eating disorders, drug addiction and use as a substitute for psycho-stimulant self-administration.

None of the background art disclosures show how chiral enantiomers of the nornicotine compounds may be used for the treatment of dopamine-related conditions and disease states. The chiral enantiomers of the nornicotine compounds of the present invention overcome deficiencies in prior treatments for dopamine-related conditions and disease states.

DESCRIPTION OF THE INVENTION

It is an object of the present invention to provide a method of treating dopamine related conditions and disease states comprising administering an effective amount of a composition comprising a compound selected from the group consisting of S-(−) nornicotine or R-(+) nornicotine, and their free base forms, inorganic acid salts and organic acid salt. The acid salts of S-(−) nornicotine or R-(+) nornicotine are selected from the group consisting of hydrochloride, hydrobromide, perchlorate, ascorbate, sulfate, tartrate, fumarate, citrate, malate, lactate, aspartate, mesylate, benzenesulfonate and proprionate, or mixtures thereof. Consistent with the invention the dopamine related conditions and/or disease states may be selected from, but not limited to myasthenia gravis, Parkinson's disease, Alzheimer's disease, schizophrenia, eating disorders, drug addiction and use as a substitute for psycho-stimulant self-administration.

The drug addiction may be a drug selected from, but not limited to nicotinic agonists, cocaine, amphetamines, caffeine, phencyclidine, opiates, barbituates, benzodiazepines, cannabinoids, hallucinogens and alcohol.

The composition used in the method of treatment of the invention may comprise a pharmaceutical carrier, and includes pharmaceutical formulations in a form of delivery selected from the group consisting of oral, transdermal, transnasal, rectal, sublinguinal, subdermal, intraocular and inhalation smokeless delivery.

Another object of the invention is to provide a method of displacement of nicotine from nicotinic receptor sites in the brain comprising administering an effective amount of S-(−)-nornicotine or R-(+)-nornicotine to cause displacement of nicotine from nicotinic receptor sites in the brain.

Still another object is to provide a method of obtaining release of dopamine from presynaptic terminals in neuronal tissue in a stereoselective and receptor-mediated manner comprising administering an effective amount of S-(−)-Nornicotine or R-(+)-Nornicotine to obtain dopamine release.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF DRAWINGS

FIG. 9A–9F show MEC (100 µM) or DHβE (10 µM inhibit norNIC-evoked [$^3$H] overflow from [$^3$H] preloaded rat striatal slices. Experiments were performed as described in FIG. 8. Total [$^3$H] overflow (top panel), total [$^3$H] overflow as % of norNIC-control (middle panel) and MEC-sensitive or DHβE-sensitive [$^3$H]overflow (bottom panel) are illustrated.

FIG. 11 shows COT evokes a concentration dependent increase in 3H overflow from rat striatal slices preloaded with 3HDA. *P, 0.05, N=6 rats.

DISCLOSURE OF THE INVENTION

The present invention provides a means to counteract the craving of individuals for drugs of abuse including: nicotinic agonists, cocaine, amphetamines, caffeine, phencyclidine, opiates, barbiturates, benzodiazepines, cannabinoids, hallucinogens, alcohol; for the treatment of neurodegenerative disorders such as Parkinson's disease, myasthenia gravis; for the treatment of schizophrenia; eating disorders, ulcerative colis, stomach ulcers and for weight control in obesity.

Experiments were necessary to elucidate the contribution nornicotine enantiomers make and their neuropharmacological effects as compared to other nicotine derivatives.

The present inventors have discovered the following:

1. S-(−)-Nornicotine and R-(+)-Nornicotine cause displacement of nicotine from nicotinic receptor sites in the brain.
2. S-(−)-Nornicotine and R-(+) nornicotine release dopamine from presynaptic terminals in neuronal tissue in a stereoselective and receptor-mediated manner.
3. Dopamine is a neurotransmitter involved in reward pathways in the brain; and loss of dopaminergic neurons is responsible for neurodegenerative disease states, i.e., myasthenia gravis, Parkinson's disease.
4. The pathophysiology of dopaminergic systems in brain is implicated in D-amphetamine and S-(−)-nicotine, schizophrenia, and individuals diagnosed as schizophrenics have been documented to have a high incidence of nicotine self-administered.
5. Dopaminergic drugs have been shown to be effective in the treatment of eating disorders and in controlling body weight, and withdrawal from nicotine increases body weight in individuals attempting to cease their smoking habit.
6. Chronic administration of S-(−)- or R-(+) nornicotine in vivo activates the mechanism involved in behavioral sensitization to psycho-stimulants, which is believed to correlate with craving in humans.
7. In behaviorally active doses, S-(−) nornicotine has no adverse effective on hemodynamic function in conscious animals, suggesting a safe drug.
8. In a drug discrimination paradigm, S-(−)-nornicotine has a drug behavioral profile similar to S-(−)-nicotine.
9. In a drug self-administration paradigm, S-(−)-nornicotine substitutes for amphetamine self administration in rats.

These findings are substantiated by the experimentation set forth below.

EXAMPLE 1

Figure 3:
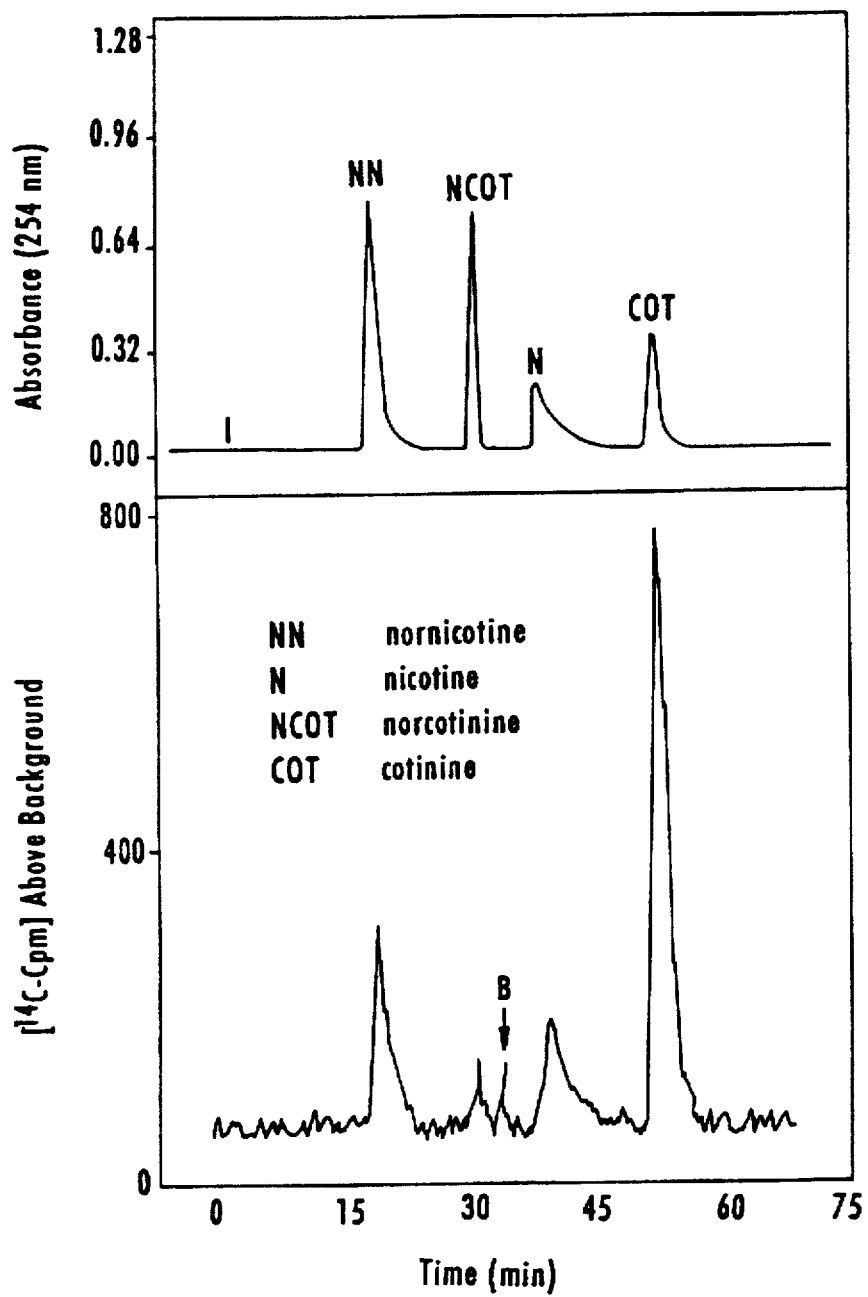
FIG. 3 shows NIC and four NIC metabolites have recently been detected in rat brain 4 hr after s.c. injection of |2'−$^{14}$C]NIC.
Figure 4B:
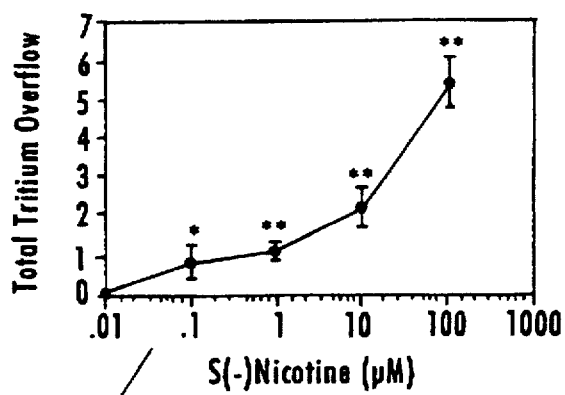
FIG. 4A–4F show, in a concentration-dependent manner, NIC (left) and norNIC (right)-evoke an increase in [$^3$H] overflow from [$^3$H]DA-preloaded rat striatal slices, but fail to produce a plateau in response. Insets illustrate the response to the low concentration range.
Figure 4A:
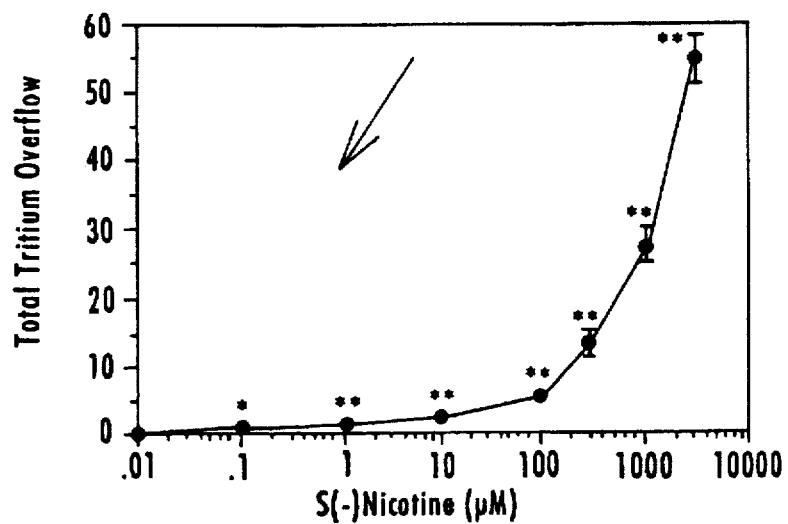
Figure 4C:
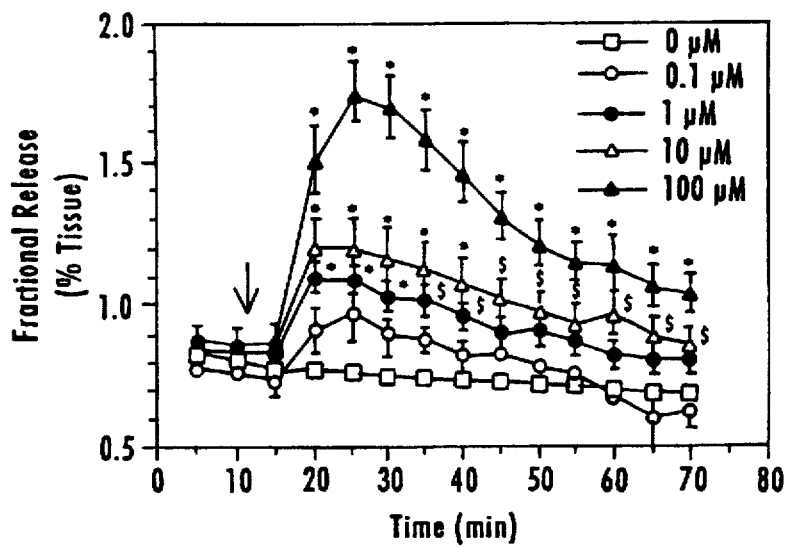
Figure 4E:
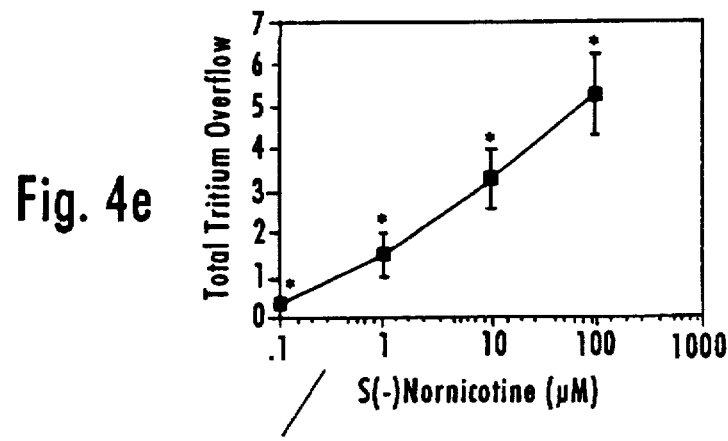
Figure 4D:
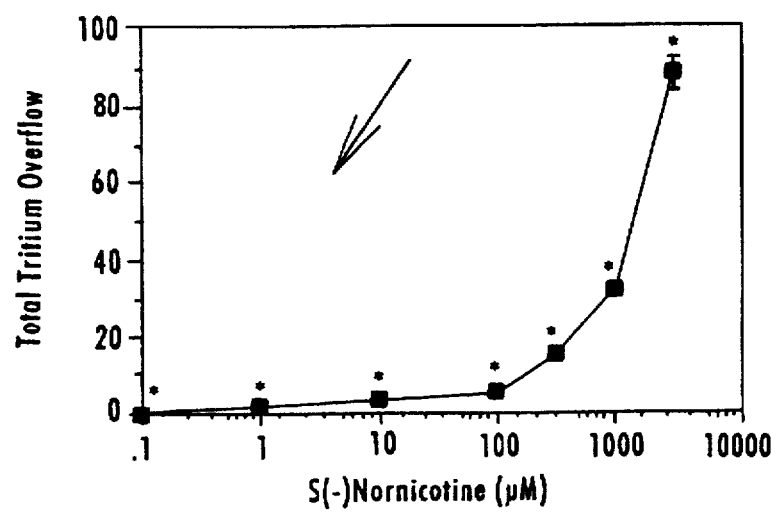
Figure 4F:
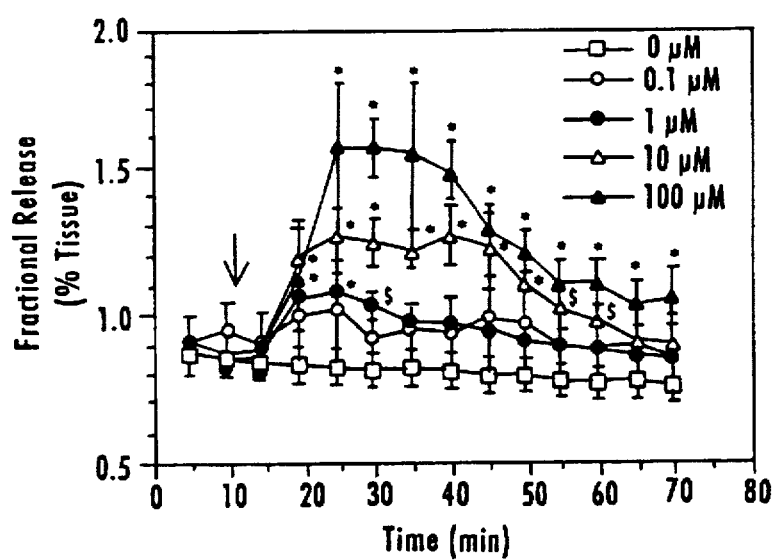

NIC metabolism studies involving HPLRC analysis invariably utilize NIC with a radiolabel (i.e., [$^3$H], [$^{14}$C] or [$^{11}$C]) incorporated in the methyl group. However N-demethylated NIC metabolites (norNIC and norCOT) cannot be detected after injection of such radionuclides, since the label is lost in the formation of these metabolites. NIC and four NIC metabolites have recently been detected in rat brain 4 hr after s.c. injection of [2'−$^{14}$C]NIC (FIG. 3, Table I). Three of these metabolites have been identified as COT, norNIC and norCOT. A fourth minor metabolite (Peak B) has not been completely identified but appears to be an N-demethylated metabolite, since it is not detected in the [$^3$H-N-methyl]NIC studies. In agreement with previous reports, COT was found to be a major metabolite of NIC in brain. NorNIC, a pharmacologically active NIC metabolite, is also present in significant amounts in brain and is believed to be formed from central N-demethylation of NIC.

NorCOT, a minor CNS metabolite of NIC, is formed in brain via 5'-C-oxidation of norNIC, since it cannot be detected in brain after s.c. administration of [G-$^3$H] COT, and therefore, is unlikely to originate from COT N-demethylation. 3-HydroxyCOT and its glucuronide conjugate were not detected as metabolites of either NIC or COT in brain, even though these are major biotransformation products in the periphery (Crooks, 1993). Several additional peaks were observed in 4-hr brain supernatants after acute [2'−$^{14}$C]NIC administration, but in amounts below the limits of automated detection. These peaks may increase significantly following chronic NIC administration, especially if CNS efflux is low and accumulation results.

In summary, these results establish for the first time the presence of norNIC and norCOT in brain following peripheral NIC administration, and indicate that the choice and position of radiolabel is a critical determinant of the number and amount of NIC metabolites observed in brain after NIC administration.

Thus, the present identification of pharmacologically active NIC metabolites in brain following peripheral NIC administration, provides evidence in support of the contention that metabolites of NIC, such as norNIC, contribute to the CNS effects of tobacco product usage, and affords new information pertinent to our understanding of the fundamental processes involved in NIC's neurochemical and behavioral effects. It is, therefore, important that the complete time course of NIC metabolite accumulation in brain be determined both in acute and chronic NIC administration studies.

EXAMPLE 2

In vitro pharmacological effects of NIC are generally investigated using either striatal slices or synaptosome preparations preloaded with [$^3$H] DA. NIC-evoked [$^3$H] overflow is obtained routinely in the presence of nomifensine (10 µM; a DA uptake inhibitor) and for pargyline (10 µM, a monoamine oxidase inhibitor) in the superfusion buffer, such that [$^3$H]overflow represents primarily [$^3$H]DA rather than [H]DA-metabolites (Zumstein et al., 1981, Hoffmann and Cubeddu, 1982, Dwoskin and Zahniser, 1986, Rapier et al., 1988), and for this reason, [$^3$H]overflow also will be referred to as [$^3$H] DA release in the proposal. NIC concentration-response curves generated with these preparations have revealed different patterns of NIC effect. FIG. 4 illustrates concentration-dependent, NIC-evoked [$^3$H]overflow from [$^3$H]DA-preloaded rat striatal slices (Teng et al., 1996). The increase in NIC-evoked DA release is in agreement with observations of others using rat striatal slices (Westfall et al., 1987, Izenwasser et al., 1991, Sacaan et al., 1995).

Figure 5B:
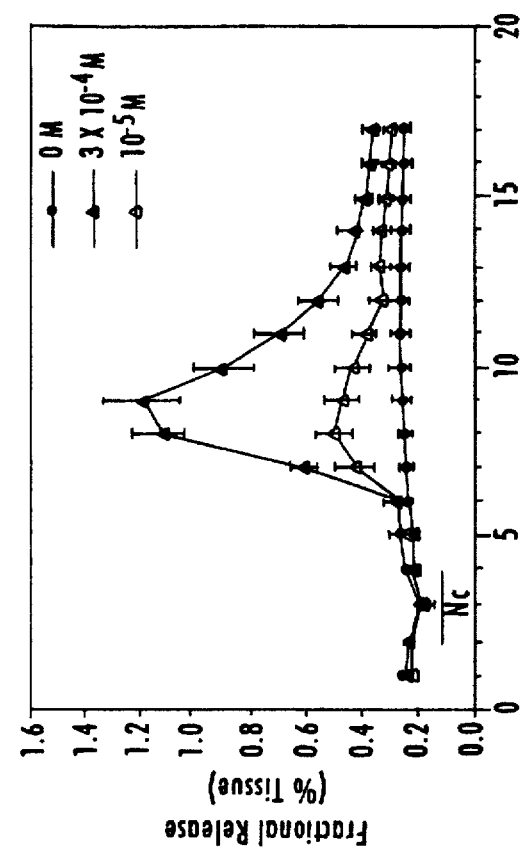
FIG. 5A–5C show a time course (top 2 panels) and concentration-dependent NIC-evoked [$^3$H] overflow (bottom panel) from [$^3$H] DA-preloaded rat striatal slices in response to a 2-min exposure. NIC exposure indicated by the bar under time course. Note: 1-min sample collection period. Plateau in [$^3$H] overflow observed at 30 mM (not shown). N=4 rats.
Figure 5C:
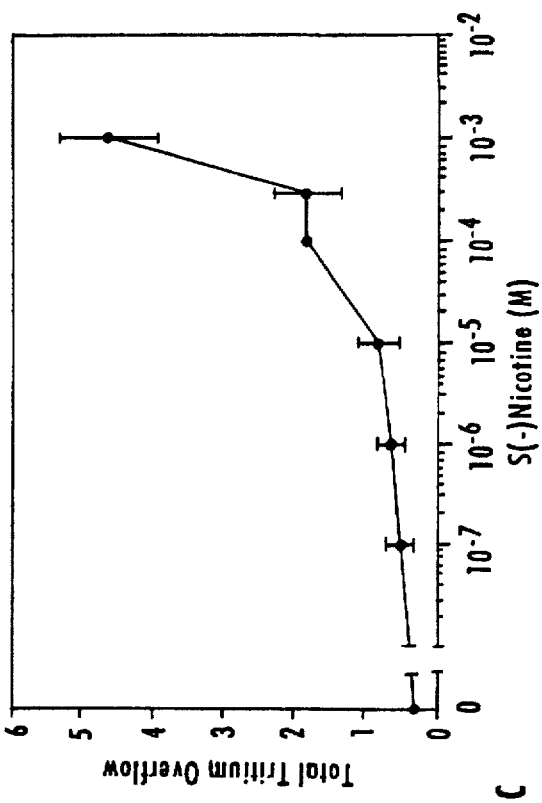
Figure 5A:
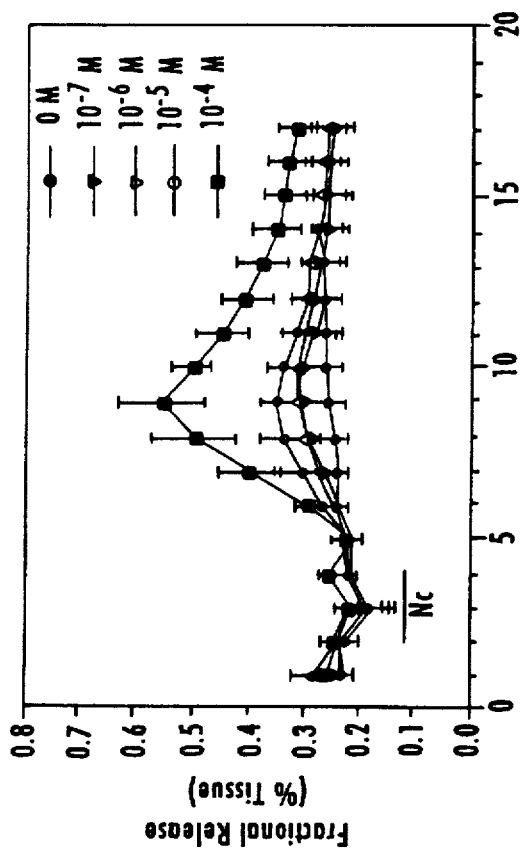

In the complete time course of the effect of 60-min exposure to NIC (1–100 µM), the peak effect was observed at 10–15 min and release returned to basal levels by 30–60 min (FIG. 4, bottom panel). Studies using synaptosomes generally use a shorter NIC exposure period (pulse, 3–10 min) and typically show a rapid peak response and rapid return to basal values (Grady et al., 1994, Rowell, 1995). FIG. 5 illustrates that when striatal slices are exposed to a 2-min NIC exposure period, the peak response is considerably broader than that seen in synaptosomal studies. Factors such as differences in the timing and pattern of response may be due to differences in one or more of the following parameters, i.e., species, tissue preparation, drug-exposure duration, and superfusion flow rate.

Thus, duration of NIC exposure is not responsible for the difference in the pattern of DA release in these two preparations. The slower and more prolonged response with slices may in large part be due to diffusion of drug, because of the presence of significant barriers to drug permeation, as a result of intact cellular connections in this preparation. Also, FIG. 4 illustrates the return of fractional [$^3$H]release towards basal levels despite the continued presence of NIC in the superfusion buffer, indicative of receptor desensitization.

fused for 60 min in order to obtain the full effect of each concentration, such that release peaked and returned to baal levels during continued NIC exposure. Shorter exposure periods lead to a truncation of the full response (FIG. 5).

In the Izenwasser et al. (1991) and Sacaan et al. (1995) studies, the striatal slices were exposed to NIC for 3–10 min and superfusate samples were collected for 10–30 min. Since in the latter studies time courses were not provided, it is possible that the plateau in the response observed resulted from a truncation of the full effect of NIC exposure, because (i) the 30 min collection period may not have included the complete response (i.e. a return to basal), and (ii) the relatively short exposure (3 min) may not have allowed for the maximal response of the tissue, particularly at the higher concentrations, to have occurred.

EXAMPLE 4

In studies using rat and mouse striatal synaptosomes, a similar discrepancy is apparent with regard to the NIC concentration-effect curve. Several groups of investigators report a plateau in the curve at concentrations between

TABLE 1

| | | NIC and metabolites in brain 4 hrs after s.c. injection of radiolabelled NIC | | | | | |
|---|---|---|---|---|---|---|---|
| | | Percent of Total Radiolabel[a] | | | | | |
| Radiolabelled NIC | N[b] | Peak A | NIC | norNIC | COT | norCOT | Peak B |
| [$^3$H—N-Methyl]-NIC[e] | 5 | 31.1 ± 2.97[c] | 29.2 ± 5.63 | 0.0 ± 0.0 | 39.6 ± 3.89 | 0.0 ± 0.0 | 0.0 ± 0.0 |
| [$^{14}$C-2']-NIC[e] | 4 | 0.0 ± 0.0 | 24.2 ± 2.94 | 15.1 ± 2.54 | 60.8 ± 0.63 | —[d] | 0.0 ± 0.0 |
| [$^{14}$C-2']-NIC[f] | 4 | 0.0 ± 0.0 | 14.2 ± 3.30 | 16.5 ± 2.04 | 62.9 ± 5.27 | 4.15 ± 0.48 | 2.33 ± 0.12 |

EXAMPLE 3

The present studies use striatal slices superfused with various concentrations of NIC or norNIC for prolonged periods. There are inconsistencies in the literature as to whether or not a plateau is observed in the NIC concentration-response curve. Westfall, et al. (987) using slices and a short (5-min) exposure period failed to observe a plateau. The present inventors have obtained similar results (FIG. 4 and 5, top panel), with either prolonged or short NIC exposure, respectively. In contrast, in a recent study by Sacaan et al. (1995), the concentration-response curve for NIC-evoked [$^3$H] overflow from [$^3$H]DA-preloaded rat striatal slices was observed to reach a plateau between 10 and 100 µM, and the EC 50 value was determined to be 3.7 µM. Several phenomena were suggested as potential contributors to the bell-shaped concentration-response curve, including receptor desensitization, nonspecific (e.g. local anesthetic) effects at very high concentrations, and release of neurotransmitters (e.g.γ-aminobutyric acid) that inhibit DA release. Izenwasser et al. (1991), also using rat striatal slices (i.e., minces), observed a plateau in the NIC concentration-response curve, but at much lower concentrations (0.1 µM, 10-min exposure period and 10-min collection period) than observed by Sacaan et al. (1995). Inconsistencies, with regard to a plateau in the response to NIC may be due to the fact that the tissue preparation was the rat striatal slice, however, variations in experimental conditions are evident, including slice thickness, volume of the superfusion chamber flow rate of superfusion buffer, duration of NIC exposure, and duration of superfusate collection.

FIG. 4 and 5 illustrate that duration of NIC exposure is not a factor that contributes to the inconsistency in the pattern of the concentration-response curve. In FIG. 4, NIC was super- 1–100 µM (Rapier, et al., 1990; El-Bizri and Clarke, 1994; Rowell et al. 1987; Rowell, 1995). In agreement with the present inventors (FIG. 4), Grady et al. (1992) also failed to observe a plateau in the concentration-response curve for NIC-evoked [$^3$H] overflow from [$^3$H]DA-reloaded mouse striatal synaptosomes using concentrations of up to 5 mM NIC and 1 min exposure. In a later study (Grady et al., 1994), a plateau was reported and an EC50 value for NIC was calculated to be 0.33 µM when the data were presented as peak DA release. However, these studies were performed over a lower concentration range (0.1–30 µM, within a flatter region of the curve from their original study) and a longer exposure period (10 min) than was originally investigated. In the Grady et al. (1992) study, a maximal response was defined as one that was insensitive to MEC inhibition.

Using this approach, the EC50 value for NIC-stimulated, MEC-sensitive [$^3$H]overflow was 0.48 µM Grady et al. (1992) interpreted their results to indicate that the full concentration-response represented both specific low-concentration range and nonspecific high-concentration range effects. It is apparent that observation of a maximal response and determination of an EC50 value for NIC may be dependent upon the experimental conditions, parameters and preparations used. Nevertheless, the nicotinic receptor-mediated portion of the response can be determined by sensitivity to nicotinic-receptor antagonists.

Reasonably good agreement with regard to pharmacological parameters (e.g. EC50) has been obtained with NIC either when a plateau (maximal response) was observed, or when the maximal response was defined by antagonist sensitivity or peak response, either using slice or synaptosomal preparation. The slice preparation has many significant advantages, i.e., its intact nature, its enhanced viability (FIG. 6), and its value for the study of neurotransmitter interactions. Furthermore, studying DA release in synaptosomal preparations does not provide a significant improvement in time resolution to approximate that observed in electrophysiological studies.

Figure 7:
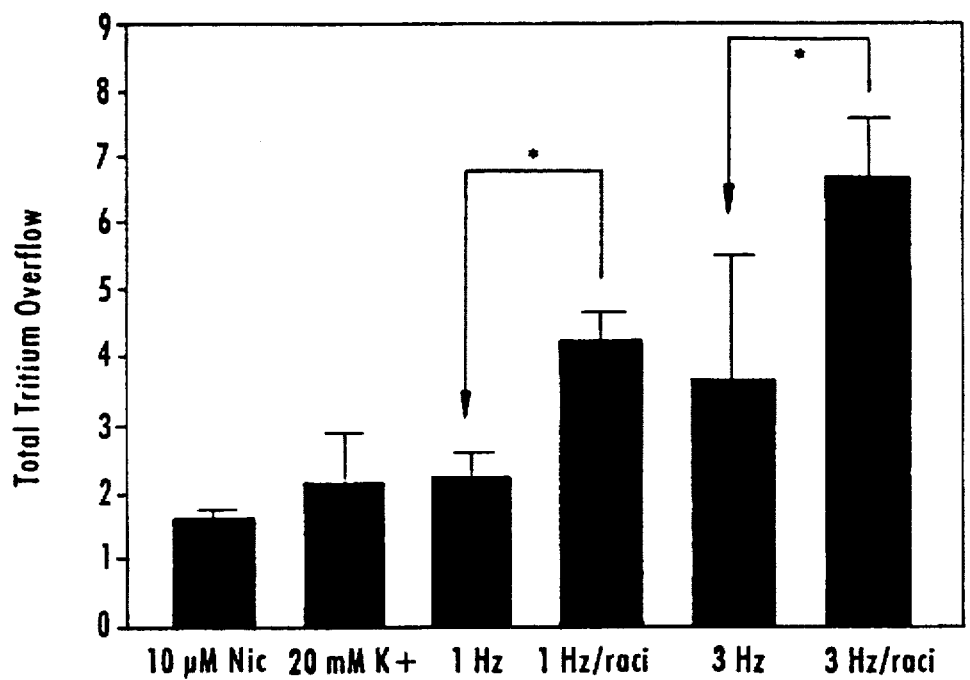
FIG. 7 shows NIC (10 µM)-evoked [3H]overflow is in a physiologically relevant response range. Rat striatal slices were depolarized with 10 µM NIC, 20 mM K+ or 1 Hz, 60 pulses or 3 Hz, 180 pulses electrical field stimulation. Raclopride (1 µM)was added to the superfusion buffer 20 min prior to electrical stimulation. *P.0.05, paired t-test. N=4.

The absolute amount of total [$^3$H]overflow in response to a low NIC concentration (e.g. 10 µM) is in the physiologically relevant range, since it was not significantly different from the response to depolarization with either 20 mM K+ or 1 Hz, 60 pulses electrical-field stimulation (FIG. 7). Also, raclopride, a DA autoreceptor antagonist, increases overflow evoked by a 1 or 3 Hz stimulation, i.e., the DA autoreceptor is active over this response range indicating physiological relevance. When the stimulus evokes a response of greater magnitude, autoreceptor function is not observed, since DA floods the extracellular space, setting up conditions which are probably nonphysiological (Dwoskin and Zahniser, 1986).

Thus, even though the response to low NIC concentrations appears relatively small when compared to that after high concentrations (FIG. 4), the response to low concentrations (and to other typically used depolarizing stimuli) is significant, reliable, reproducible, physiologically relevant, and receptor-mediated.

(±) norNIC has been shown to evoke a concentration dependent increase in [$^3$H]overflow from H]DA-preloaded mouse striatal synaptosomes, however, it should be noted that a racemic norNIC was used in this study (Grady et al., 1992), not distinct enantiomers. The present inventors report that the S(−) enantiomer of norNIC (0.1–100 µM, 15 min exposure) evokes a concentration-dependent and Ca$^{++}$-dependent increase in endogenous DA release from rat striatal slices (Dwoskin et al., 1993). Similar Ca$^{++}$-dependency has been observed with NIC-evoked DA release (Giorguieff-Chesselet et al., 1979, Westfall et al., 1987, Rapier et al., 1988; Sacaan et al., 1995).

FIG. 4 illustrates the effect of a wider range of concentrations (0.1 µM–3 mM) of norNIC on [$^3$H]overflow from [$^3$H]DA-preloaded rat slices, and the complete 60-min time course of the response to each concentration. The pattern of the concentration-response curve for norNIC appears similar to that for NIC. Thus the results are indicative of receptor desensitization with norNIC during prolonged exposure with low concentrations.

EXAMPLE 5

Since a plateau in the norNIC concentration-response curve was not observed at concentrations up to 3 mM (FIG. 4), nicotinic receptor mediation was assessed by determining the sensitivity to nicotinic antagonists. MEC has been reported to be a noncompetitive inhibitor of the N-methyl-D-aspartate (NMDA) receptor, acting at the MK-801 site within the channel (Reynolds and Miller, 1988; Snell and Johnson, 1989, Court et al., 1990). Thus, it is important to determine if the effect of norNIC was also inhibited by the competitive nicotinic receptor antagonist, DHβE (Vidal and Changeux, 1989, Alkondon and Albuquerque, 1991; Mulle et al., 1991) to verify nicotinic receptor mediation.

In the present studies, MEC (0.01–100 µM) did not alter [$^3$H]DA release itself, whereas high concentrations (100 µM of DHβE evoked the release of [$^3$H]DA itself, and thus, was not used to investigate nicotinic receptor-mediated mechanisms of NIC and norNIC.

In a concentration-dependent manner, both MEC and DHβE robustly inhibited MC-evoked [$^3$H] overflow from [$^3$H] DA-preloaded striatal slices (FIG. 8), in good agreement with the results of previous studies using rat striatal slices or synaptosomes (EI-Bizri and Clarke, 1994; Sacaan et al., 1995). Moreover, MEC and DHβE also effectively inhibited [$^3$H]overflow evoked by low concentrations (<100 µM) of norNIC, but both were ineffective in inhibiting the response to high concentrations (100 µM–3 mM) of norNIC (FIG. 9). The overall depression of the norNIC concentration-response curves in the presence of MEC and the shift to the right of the concentration-response curve in the presence of DHβE are consistent with noncompetitive and competitive antagonism, respectively. MEC-sensitive and DHβE-sensitive concentration-response curves revealed maximal responses of norNIC (FIG. 9). EC50 values for norNIC stimulated, MEC-sensitive and DHβE-sensitive [$^3$H]overflow were 2.54+0.67 µM and 0.88±0.31 µM (P>0.05, t-test), respectively. Interestingly, norNIC has similar potency to NIC in the DA release assay. Thus, these results suggest that the effect of norNIC at concentrations <100 µM is the result of stimulation of nicotinic receptors, and that high concentrations of norNIC release DA via a nonselective mechanism that is insensitive to MEC and DHβE.

In summary, norNIC evokes DA release from rat striatal slices in a concentration-dependent manner, and nicotinic receptor desensitization occurs when slices are superfused with low concentrations of norNIC. Under these conditions, the effect of norNIC is stereoselective and is antagonized by MEC and DHβE, suggesting that norNIC at low concentrations acts at nicotinic receptors to evoke DA release from rat striatal slices.

Concentrations (0.1 µM) of norNIC, within the low range found to release DA (FIG. 4), have been detected in brain 4 hr after administration (s.c.) of [2'-$^{14}$C]NIC to rats (Crooks et al., 1995). Thus, these low concentrations of norNIC are pharmacologically relevant with regard to brain concentrations following smoking and peripheral nicotine administration in man.

EXAMPLE 6

In additional studies, the inventors demonstrate that S-(−)- norNIC produces behavioral sensitization following repeated administration, whereas R(+) norNIC does not. Although, following chronic administration, R(+) norNIC did not produce an overt behavioral effect, R(+) norNIC enabled an enhanced response to NIC challenge, such that the rats behaved as though they had been administered NIC (FIG. 12, results from studies with R(+) norNIC and NIC illustrated only). Saline, NIC (I mg/kg), norNIC (0.3–10 mg/kg) or R(+) norNIC (0.3–10 mg/kg) was administered peripherally (s.c., 8 injections once every 48 hrs) to groups of rats and locomotor activity was assessed for 50 min immediately after each injection. The behavioral response to each compound was notably complex. Following acute injection of NIC, there was a transient (lasting 10 min) hypoactivity followed by hyperactivity late in the session, when the data were compared to the saline-injected group. When activity was collapsed across time, activity in the acute NIC group was not different from the saline group. However, following repeated NIC administration only hyperactivity was observed across the time course of the session (i.e., tolerance to the hypoactive phase, and sensitization to the hyperactive phase of the behavioral response were observed).

Interestingly, after both acute and chronic administration, an enantioselective effect of norNIC on activity was observed. Acute administration low dose of norNIC produced an early (lasting 20 min) hyperactive phase, in contrast to NIC; and when the data were collapsed across the session, an increased activity was observed compared to saline controls. However, the high dose of norNIC produced an early (lasting 10 min) hypoactivity similar to NIC, and the cumulated results indicated significant hypoactivity, as well. In contrast, activity following acute administration of the low dose of R(+) norNIC was not different from saline, whereas, the high dose resulted in early (lasting 20 min) hypoactivity, which in contrast to NIC did not rebound later in the session.

Thus, the acute R(+) norNIC administration resulted in an inverted-U shaped dose response curve. Interestingly, following chronic administration of norNIC, behavioral sensitization was observed, similar to NIC, and when this group was challenged with NIC, 48 hrs following the last dose of norNIC, cross-sensitization was observed (activity after NIC challenge was not different from activity on the last day of repeated administration, data not shown), suggesting that a similar mechanism may be involved.

Moreover, the time course of activity and the cumulated response reveal that repeated administration of the high dose of R(+) norNIC resulted in activity not different from the saline-control group (tolerance developed to the depressant effect after acute administration), whereas activity was still depressed after chronic administration of the lowest dose of R(+) norNIC (FIG. 12).

It is important to note that the NIC group (positive control) was sensitized following repeated MC injection in this study. Surprisingly, when the R(+) norNIC group was challenged with NIC, responded as if they had received chronic NIC (i.e., there was a dose-related NIC-lnduced stimulation of activity which represents the enabling effect of R(+) norNIC). Note, as indicated by # in FIG. 12, the activity of the R(+) norNIC group after NIC challenge was significantly different from activity of the same group on the last day of repeated R(+) norNIC administration.

EXAMPLE 7

Finally, to determine if the increase in activity was due to a conditioned effect of the repeated drug administration, all treatment groups were challenged with saline 48 hrs following NIC challenge, and activity was determined immediately thereafter. Locomotor activity for all the drug treatment groups was not different from the saline control group (not shown). Thus, a conditioned response to the repeated drug administration did not contribute to the observed behavioral sensitization. A focus of this work is to determine the mechanism of the enabling effect of R(+) norNIC and of the sensitization induced by norNIC.

The present behavioral results are in agreement with the findings of Stolerman et al. (1995) who reported that acute R(+) norNIC decreased locomotor activity in rats, and that after chronic NIC, cross-sensitization to R(+) norNIC was observed.

Figure 13:
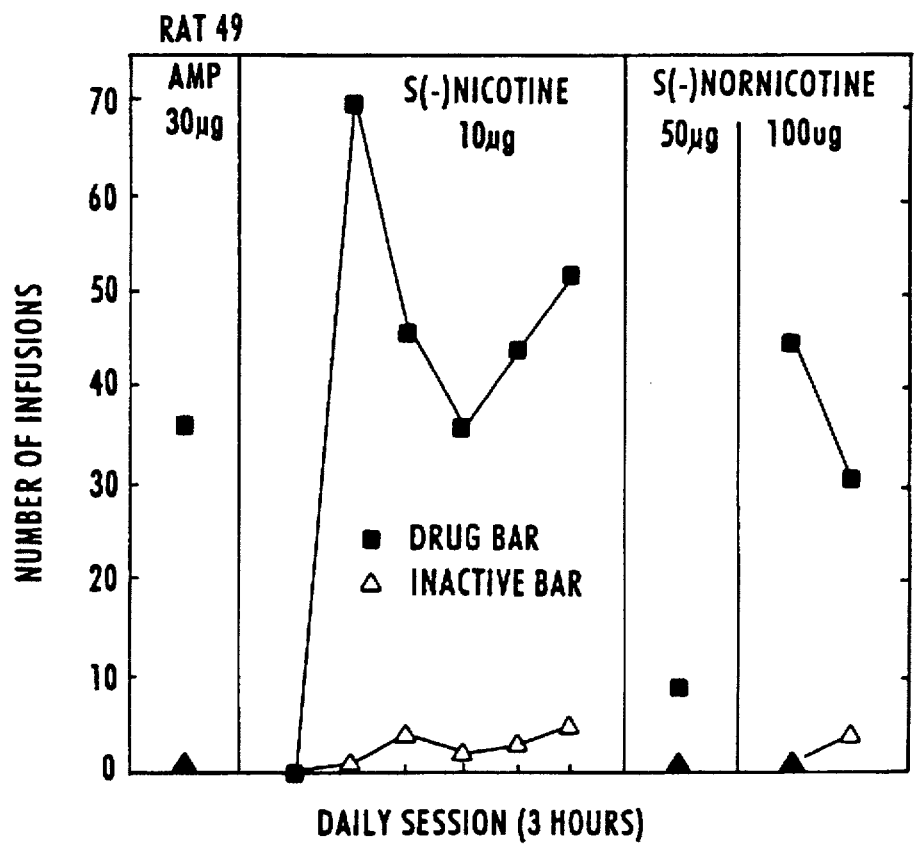
FIG. 13 shows mean percent of amphetamine-appropriate responses (top figure) and total responses (bottom figure) when amphetamine, nicotine or nornicotine were administered 15 min prior to the substitution test session.

Finally, the inventors show that norNIC, is reinforcing in rats using the drug self-administration paradigm. This evidence was obtained from a single rat with an extensive history of responding for amphetamine (AMPH, i.v., 30 μg per infusion). When NIC was substituted for MPH, responding was established and maintained over a 5-session period. Moreover, this rat also responded for norNIC (100 μg per infusion) at a rate similar to that previously obtained for AMPH and NIC (FIG. 13).

Taken together, three important conclusions can be drawn from these studies: (i) following peripheral administration of NIC, we have observed NIC metabolites (COT, norNIC, norCOT and a 4th unidentified metabolite) in brain; (ii) NIC, norNIC and COT have been shown to evoke DA release from rat striatal slices in vitro, and the norNIC effect was nicotinic-receptor mediated, in that it was MEC-sensitive, DHβE sensitive, stereo-selective and $Ca^{++}$-dependent, (iii) norNIC and R(+) norNIC, were capable of activating the neural mechanism responsible for behavioral sensitization, even though R(+) norNIC produced no overt behavioral effects after repeated administration. Since behavioral sensitization has been suggested to be dependent on activation of DA systems and since norNIC evokes DA release, these results suggest a significant role for norNIC in the behavioral sensitization produced by NIC.

EXPERIMENTAL DESIGN AND METHODS

To determine enantiomeric nornicotine use, the present inventors design studies to determine the following:

1. Nicotinic receptor upregulation and desensitization (i.e., upon exposure to nornicotine isomers).
2. The effective of chronic and acute administration of nornicotine enantiomers on dopamine release from nucleus accumbens (mesolimbic dopamine reward pathways).
3. Blood pressure effects of nornicotine enantiomers in conscious animals.
4. Dopamine uptake in vivo in neuro-tissue (Dopamine terminal areas) after acute and chronic treatment with nornicotine enantiomers.
5. Behavioral effects—to determine if nornicotine enantiomers are self-administered in laboratory animals. Work indicates that S-(−)-nornicotine is self-administered in rats with a history of stimulant use.
6. Nicotinic receptor sub-type involvement in the nornicotine enantiomer responses.
7. Localization of the nicotinic receptor sub-type involved in nornicotinine enantiomer binding in CNS tissue.
8. Upregulation of nicotinic receptors following chronic nornicotine enantiomer administration.
9. Nornicotine enantiomer substitution for psychostimulants and other drugs of abuse in self-administration and drug discrimination paradigms.
10. Neuroprotective effects of nornicotine enantiomers following dopaminergic lesion in the brain.
11. Effect of nornicotine enantiomers on food intake in animal models for obesity.
12. Assess the ability of nornicotine enantiomers to modulate the action of antipsychotic medications on dopamergic function.

Determine the time course and concentration of naturally occurring NIC and its metabolites (COT, norNIC and norCOT) in brain and plasma following acute and chronic administration of [2'-$^{14}$C]NIC and determine if the time course of metabolite accumulation correlates with the time course of MC-induced behavioral sensitization.

It appears that NIC metabolites which accumulate with a time course that correlates with the development of behavioral sensitization to NIC have a role in eliciting sensitization to NIC. The inventors have detected NIC, COT, norNIC and norCOT in brain 4 hr following acute s.c. injection of (±)[2'-$^{14}$C]NIC. S(−) [$^3$H] -N-methyl]NIC is unsuitable for studying brain metabolism of NIC, since nor-metabolites (i.e., demethylated metabolites) cannot be detected due to [$^3$H]-loss during metabolism (Crooks et al., 1995b, AP 7). Thus, commercially available (±)[2'-$^{14}$C]NIC was used to determine NIC metabolites present in brain. This form of radiolabelled NIC provides a metabolically stable [$^{14}$C]-label which allows measurement of all potential NIC metabolites.

EXAMPLE 8

Nicotine has been suggested to produce its locomotor stimulant and reinforcing effects by activating nicotinic receptors in the mesolimbic dopaminergic system. These effects may not be due solely to nicotine, but result at least in part from effects of active nicotine metabolites. In the present study, S(−) nicotine (1 mg/kg), R(+) nornicotine (1–10 mg/kg), S(−) nornicotine (1–10 mg/kg), or vehicle (saline) were administered s.c. to groups of rats (n=6) acutely or repeatedly (8 injections once every 48 hrs). Locomotor activity was measured during 50 min sessions immediately following drug or vehicle administration. Acute administration of S(−) nicotine produced a short-lasting decrease in locomotor activity early in the behavioral session; and then later in the session, an increase in activity was observed. Thus, when averaged over the entire session, activity was not different from control. Acute administration of R(+) nornicotine produced a dose-response curve with an inverted-U shaped function; whereas, acute administration of S(−) nornicotine produced a biphasic dose response curve with a increase in activity at the low dose and a decrease in activity at the high dose. Thus, enantio-selective effects of nornicotine were observed after acute administration. Repeated administration of S(−) nicotine produced tolerance to the depressant effect and sensitization to the stimulatory effect of S(−) nicotine.

Following repeated administration of R(+) nornicotine, tolerance to the depressant effect of the high dose, but not the low dose, was observed. In contrast, to S(−) nicotine, behavioral sensitization was not observed following repeated R(+) nornicotine. Chronic R(+) nornicotine (0.3–10 mg/kg) did not produce behavioral sensitization. Following repeated administration of S(−) nornicotine, tolerance to the acute effects were observed; and moreover, behavioral sensitization was observed following the high dose. Chronic S(−) nornicotine (10 mg/kg) produced behavioral sensitization, whereas lower doses did not. Thus sensitization was observed following S(−) nornicotine, but not following R(+) nornicotine. When the groups were challenged with nicotine (1 mg/kg), rats chronically administered R(+) nornicotine (3 and 10 mg/kg) or S(−) nornicotine (3 and 10 mg/kg) responded as if administered nicotine, i.e., behavioral sensitization was then demonstrated in the R(+) nornicotine group and cross-sensitization was observed in the S(−) nornicotine group. When the groups were challenged with saline, increases in locomotor activity were not observed, i.e., the increase in locomotor activity was not due to a conditioning effect. Thus, chronic S(−) nornicotine (10 mg/kg) produced behavioral sensitization, and cross-sensitization to S(−) nicotine was observed. In contrast, following repeated R(+) nornicotine administration, sensitization was not observed. Moreover, chronic R(+) nornicotine administration enabled sensitization to S(−) nicotine Thus, although R(+) nornicotine did not overtly produce behavioral sensitization, it stimulated the CNS mechanism(s) responsible for sensitization.

EXAMPLE 9

The hypothesis tested in the present study is that CNS effects resulting from nicotine exposure are not solely due to nicotine, but result at least in part from actions of nicotine metabolites.

From a molecular view point, the structure of nornicotine suggests that it may have significant nicotinic receptor agonist properties. Recently in behavioral studies, R(+) norNIC administered to experimentally naive rats decreased locomotor activity, an effect which was blocked by mecamylamine; moreover, in rats chronically administered nicotine, R(+) nornicotine challenge increased activity, demonstrating cross-sensitization and the involvement of a common nicotinic receptor-mediated mechanism (Stolerman et al., 1995). Also, in operant behavioral studies using food reinforcement in monkeys, dogs and rats (Risner et al., 1985, 1988; Goldberg et al., 1989), both enantiomers of nornicotine were found to be active. In the present study, the ability of S(−) nornicotine and R(+) nornicotine to induce behavioral sensitization in a locomotor activity assay was investigated, and their effects were compared to that of S(−) nicotine.

Animals

Male Sprague-Hawley rats (225–250 g) from Harlan Laboratories were housed two per cage with free access to food and water.

Locomotor activity assay

Activity was recorded automatically in a wooden test-chamber measuring 30×28×43 cm high. The chamber had white walls and a wire mesh floor over pine chip bedding. Two photobeams located 4.5 cm above the floor divided the chamber into four equal quadrants. Electromechanical equipment located in an adjacent room recorded photobeam interruptions automatically. A white noise generator provided an ambient 70 dB background noise in the test room in order to minimize extraneous sounds that might influence the animal's behavior in the test chamber. Rats were habituated to the chamber for 50 min on each of three consecutive days.

Drug treatment

On the day immediately after the third habituation session, rats were randomly divided into groups (n=6/group) and were administered s.c. either S(−) nicotine (1 mg/kg), R(+) nornicotine (0.3, 1, 3 and 10 mg/kg), or vehicle (saline) to determine acute drug effects on locomotor activity. In a separate experiment, rats (n=6/group) were administered s.c. either S(−) nicotine (1 mg/kg), S(−) nornicotine (0.3, 1, 3 and 10 mg/kg), or vehicle (saline). To determine the effect of repeated drug administration on locomotor activity, drug or vehicle was administered respectively in the test-room once every 48 hrs for a total of 8 injections. After each injection, locomotor activity was recorded during a 50 min session (five 10-min blocks). On the ninth injection day (48 hrs following injection 8), each group of rats was administered a challenge dose (1 mg/kg) of S(−) nicotine in the test-room, and locomotor activity was determined immediately thereafter. On the tenth injection day, each group of rats was administered saline and locomotor activity recorded to determine potential conditioning effects of the repeated drug administration.

Results were examined by two-factor and three-factor analyses of variance with between-groups treatment factors and within-groups behavioral session and time factors. Post hoc analysis of pairwise comparisons was performed with Duncan's New Multiple Range test.

Drugs

S(−) nicotine ditartrate was purchased from Research Biochemicals Inc. (Natick, MA). S(−) nornicotine and R(+) nornicotine were synthesized in the perchlorate salt form according to an unpublished method (Crooks et al., unpublished). Drug dose was based on the salt.

EXAMPLE 10
R(+) Nornicotine Experiment: cumulated locomotor activity

The effect of acute and repeated administration of R(+) nornicotine (0.3–10 mg/kg), S(−) nicotine (1 mg/kg) or saline (vehicle) on locomotor activity cumulated across a 50-min behavioral session is shown in FIG. 12. Analysis by two-factor ANOVA revealed a significant between-groups treatment effect [F(5,30)=8.80, P<0.0001], a significant within-group effect of behavioral session [F(3,90)=26.90, P<0.0001] and a significant treatment×session interaction [F(15,90)=7.91, P<0.0001].

Acute Treatment

Acute administration of R(+) nornicotine produced a dose-response curve with an inverted-U shape for cumulated locomotor activity. Post hoc analysis revealed that following the acute administration of S(−) nicotine (1 mg/kg), locomotor activity was not different from the saline-control group (FIG. 12, top panel). Also, after acute administration of both the low (0.3 mg/kg) and high (10 mg/kg) dose of S(−) nornicotine, a significant decrease in locomotor activity was found compared to the saline-control group; whereas activity was not different from control after the intermediate doses (1 and 3 mg/kg) (FIG. 12, top panel). Thus, both a low and high dose of R(+) nornicotine produced a depression in activity.

Repeated Treatment

Figure 1:
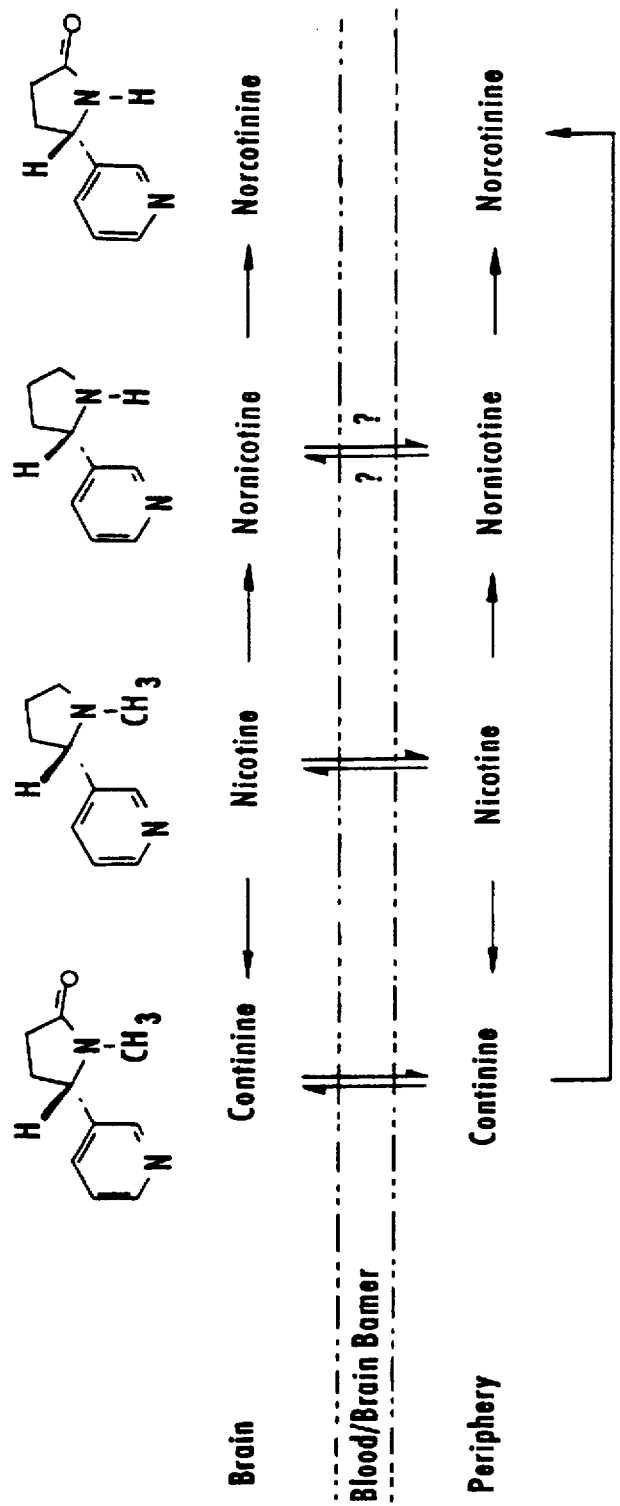
FIG. 1 summarizes the present understanding of the origin of NIC metabolites present in brain after peripheral NIC administration.

Following repeated treatment with S(−) nicotine (1 mg/kg, once every 48 hrs for 8 injections), locomotor activity was increased significantly compared to the saline-control group (FIG. 12, middle panel) and compared to the activity of the S(−) nicotine-treatment group following acute S(−) nicotine administration (FIG. 1, top panel). The S(−) nicotine-induced increase in activity reached a plateau following 4 injections of the drug (data not shown). Thus, repeated, intermittent administration of S(−) nicotine resulted in a robust behavioral sensitization.

In contrast to the behavioral sensitization induced by repeated S(−) nicotine administration, repeated administration of R(+) nornicotine did not result in behavioral sensitization. Following 8 injections of the low dose (0.3 mg/kg) of R(+) nornicotine, locomotor activity was decreased significantly compared to the saline-control group (FIG. 12, middle panel), and was not different from activity after acute administration (FIG. 12, top panel). After each of the 8 injections of the low dose, activity was not different from that after acute administration (data not shown). Thus, tolerance did not develop to the depressant effect of the low dose of R(+) nornicotine following repeated, intermittent administration. Following repeated administration of higher doses (1, 3 and 10 mg/kg) of R(+) nornicotine, locomotor activity was not different from that of the saline-control group (FIG. 12, middle panel). Of note, tolerance developed to the depressant effect of the acute administration of the 10 mg/kg dose (FIG. 12, top panel), such that activity was back to control levels after 8 injections (FIG. 12, middle panel). Tolerance was apparent after the third injection of 10 mg/kg (data not shown). Moreover, behavioral sensitization following repeated administration of R(+) nornicotine was not observed, since activity was not increased above that of the saline-control group.

EXAMPLE 11
S(−) Nicotine Challenge

When the saline-control group was challenged acutely with S(−) nicotine (FIG. 12, bottom panel), locomotor activity was not different from that after acute saline administration (FIG. 12, top panel), nor was it different from that of the S(−) nicotine-treatment group after acute S(−) nicotine administration (FIG. 12 top panel). When the S(−) nicotine-treatment group was challenged with S(−) nicotine, locomotor activity was not different from this group's activity following the last dose of the repeated regimen of S(−) nicotine treatment (FIG. 12, middle panel); however, this group's activity was significantly increased compared to the activity of the saline-control group following S(−) nicotine challenge (FIG. 12, bottom panel). Thus, behavioral sensitization was observed following repeated S(−) nicotine administration.

In the R(+) nornicotine groups, the increase in locomotor activity in response to S(−) nicotine challenge was directly proportional to the dose of R(+) nornicotine repeatedly administered. After S(−) nicotine challenge, locomotor activity in the treatment groups administered the lower doses (0.3 and 1 mg/kg) of R(+) nornicotine was not different from the saline-control group (FIG. 12, bottom panel). S(−) Nicotine challenge produced significant increases in activity in the treatment groups administered 3 and 10 mg/kg R(+) nornicotine when compared to the saline-control group; however, the activity of these groups was significantly less than that of the S(−) nicotine-treatment group (FIG. 12, bottom panel). Moreover, the activity following S(−) nicotine challenge in the treatment group repeatedly administered R(+) nornicotine (10 mg/kg) was significantly greater than this group's activity on the last day of the repeated-treatment regimen (FIG. 12, middle and bottom panels). Therefore, although R(+) nornicotine did not stimulate activity when administered repeatedly, S(−) nicotine challenge resulted in a significant increase in locomotor activity, such that behavioral sensitization was unmasked.

EXAMPLE 12
R(+) Nornicotine Experiment: time course When the time course of the drug effect on locomotor activity was analyzed, the complexity of the response to both S(−) nicotine and R(+) nornicotine was apparent. Three-factor ANOVA revealed significant main effects of treatment [F(5,28)=9.05, P<0.0001], behavioral session [F(3,84)=26.63, P<0.0001] and time [F(4,112)=335.93, P<0.0001], and moreover, a significant three-way treatment×session×time interaction [F(60,336)=4.96, P<0.0001].

Acute treatment

Figure 2:
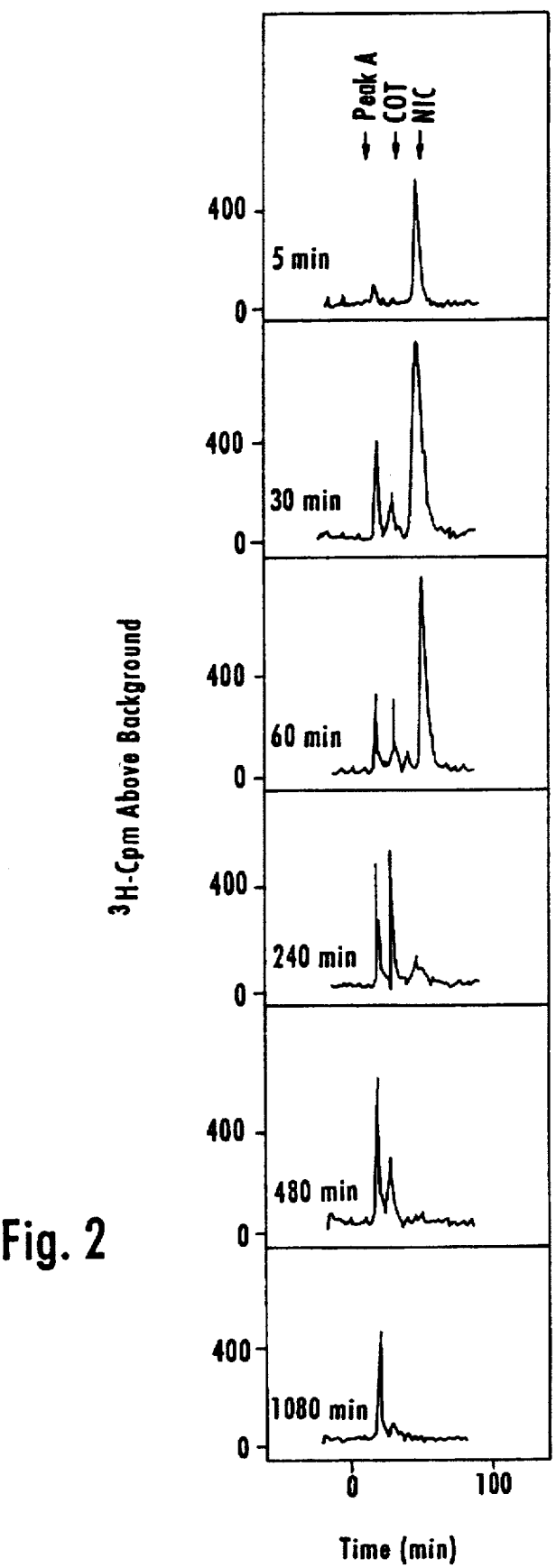
FIG. 2 shows the time course of appearance of NIC and COT in brain from representative rats is illustrated in NIC distribution to brain is rapid, maximum uptake occurring between 30–60 min.

The time course of the effect of acute administration of S(−) nicotine or R(+) nornicotine is illustrated in FIG. 2 (top panel). When the saline-control group was acutely administered saline, locomotor activity over the course of the 50-min session decreased from 167±16 to 24±12 photobeam interruptions. When compared to the saline-control group, acute S(−) nicotine (1 mg/kg) administration significantly decreased activity during the first 10 min of the session, did not alter activity from 20–40 min, and significantly increased locomotor activity during the last 10 min of the session (FIG. 2, top panel). The locomotor depression observed early in the session and the stimulation observed later, canceled each other out, such that cumulated locomotor activity after acute S(−) nicotine was not different from the saline control group (FIG. 12, top panel).

Figure 16A:
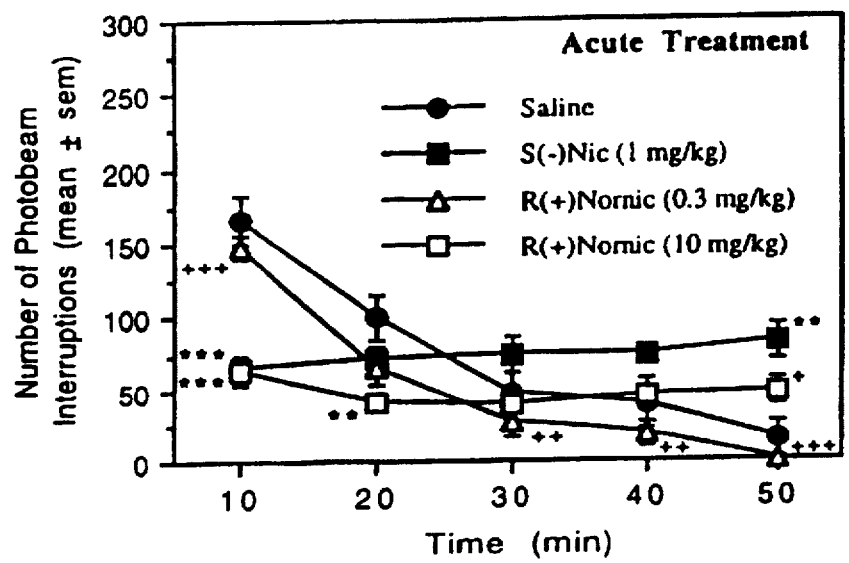
FIG. 16A and 16C show behavioral sensitization and cross-sensitization following repeated administration of S(−) nicotine or S(−) nornicotine.
Figure 16B:
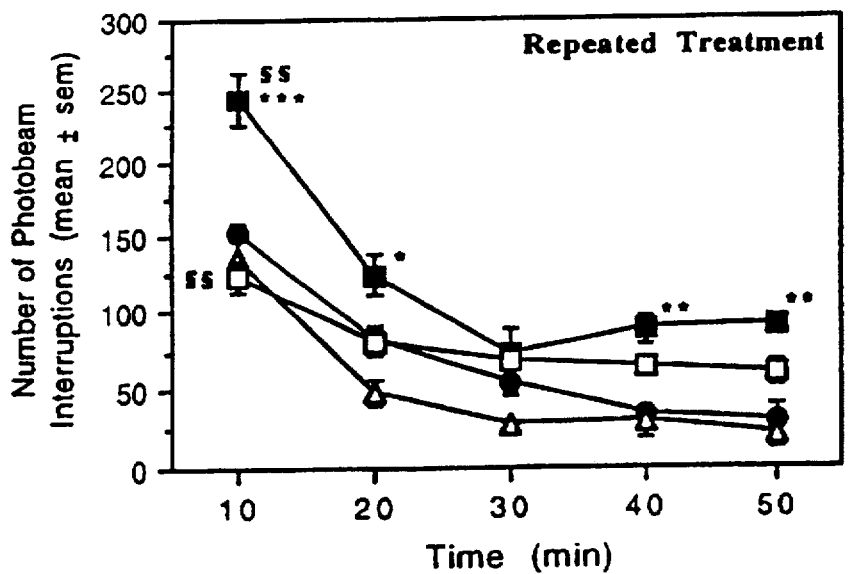
FIG. 16. Behavioral sensitization and cross-sensitization following repeated administration of S(−) nicotine or S(−) nornicotine.
Figure 16C:
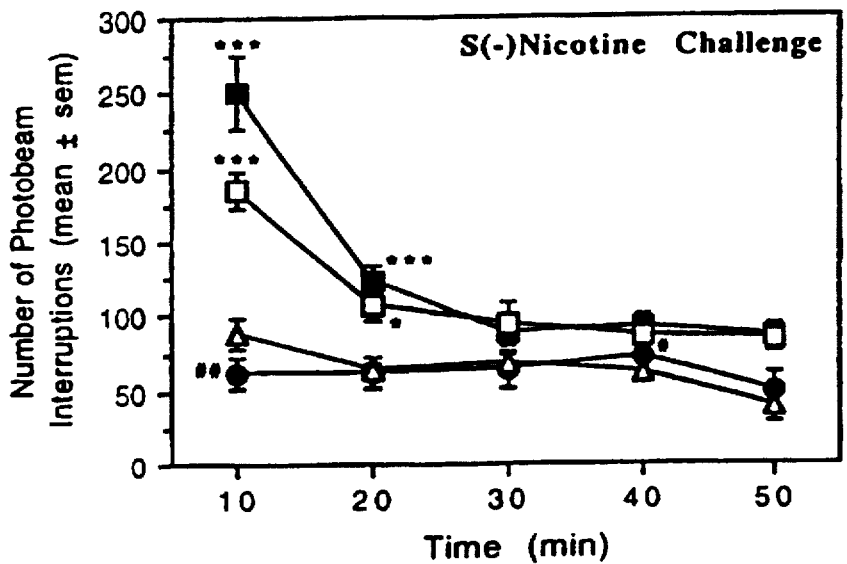

Compared to the saline-control group, acute administration of 0.3 mg/kg R(+) nornicotine consistently produced small, but not significant, decreases in locomotor activity over the time course of the session (FIG. 16, top panel); and, summed across the session, a significant cumulated decrease in activity was observed (FIG. 12, top panel). After acute administration of the higher doses (1 and 3 mg/kg) of R(+) nornicotine, locomotor activity was not different from the saline-control group over the time course of the session; except during the first 10 min of the session following administration of 3 mg/kg. in which a significant (P<0.05) decrease in locomotor activity (125±17 photobeam interruptions) compared to the saline-control group was observed (data not shown). The decrease in activity produced by 3 mg/kg of R(+) nornicotine was significantly (P<0.001) less than that produced by 10 mg/kg. Thus, early in the session, a dose-related R(+) nornicotine-induced depression of activity was observed. Following acute administration of 10 mg/kg of R(+) nornicotine, locomotor activity was significantly decreased during the initial 20 min of the session compared to the saline-control group; however, during the latter part of this session, activity was not different from the saline-control group (FIG. 16, top panel). Similar to acute S(–) nicotine, the high dose of R(+) nornicotine depressed activity early in the session; however, in contrast to acute S(–) nicotine, activity was not stimulated significantly later in the session (FIG. 16, top panel). Thus, a significant R(+) nornicotine (10 mg/kg)-induced depression of the cumulated behavioral response resulted from an initial depression in activity which was not compensated for by a later increase in activity during 10 the course of the session (FIG. 12 and 2, top panels).

Repeated Treatment

Similar to the acute administration of saline, locomotor activity decreased across the time course of the session following repeated saline administration (FIG. 16, middle panel). Furthermore, repeated administration of S(–) nicotine resulted in a significant increase in activity during the majority of the time course. Notably, tolerance developed to the decrease in locomotor activity observed during the first 10 min of the session following acute S(–) nicotine administration. Later in the session, repeated S(–) nicotine administration significantly stimulated activity. Thus, behavioral sensitization resulting from repeated, intermittent S(–) nicotine administration was observed.

EXAMPLE 13

Following repeated administration of R(+) nornicotine (0.3–10 mg/kg), locomotor activity was not different from that of the saline-control group over the entire time course of the session (FIG. 16, middle panel). Interestingly, at the 10 min time point, locomotor activity following repeated R(+) nornicotine (10 mg/kg) was significantly greater than after acute administration (FIG. 16, top and middle panel). Thus, similar to S(–) nicotine, tolerance developed to the significant behavioral depression observed during the first 10 min of the session following acute R(+) nornicotine (10 mg/kg). However, in contrast to repeated S(–) nicotine administration, R(+) nornicotine (0.3–10 mg/kg) did not stimulate activity above that of the saline-control group. Thus, repeated R(+) nornicotine did not produce behavioral sensitization.

Nicotine Challenge

Following S(–) nicotine challenge, the response of the saline-control group was similar to the response of the S(–) nicotine-treatment group following acute S(–) nicotine administration. S(–) nicotine challenge of the saline-control group resulted in a significant decrease in activity during the first 10 min of the session and a significant increase in activity at 40 min, compared with the same time points on the last day of the repeated regimen (FIG. 16, middle and bottom panels). Following S(–) nicotine challenge, the response of the S(-Inicotine-treatment group was not different from their response on the last day of the 11 repeated regimen. Locomotor activity of the S(–) nicotine-treatment group was significantly increased for the first 20 min of the session, when compared to the saline-control group acutely challenged with S(–) nicotine (FIG. 16, bottom panel). During the latter part of the session, locomotor activity of the S(–) nicotine-treatment group tended to be, but was not significantly, greater than that of the saline-control group. Thus, behavioral sensitization was observed in the S(–) nicotine-treatment group after S(–) nicotine challenge.

The increase in locomotor activity in response to S(–) nicotine challenge was directly dependent on the dose of R(+) nornicotine previously administered (FIG. 16, bottom panel). S(–) nicotine-induced stimulation of activity during the first 10 min of the behavioral session was not significant following repeated 0.3 mg/kg R(+) nornicotine treatment, but was significant (P<0.001) and dose-dependent following the higher doses (1–10 mg/kg) of R(+) nornicotine (FIG. 16, bottom panel, and data not shown graphically for 1 and 3 mg/kg; 127±12 and 136+32 photobeam interruptions, respectively). Furthermore, stimulation of activity induced by S(–) nicotine challenge was more prolonged (lasting 20 min) for the group administered the highest dose of R(+) nornicotine.

EXAMPLE 14

S(–) nornicotine Experiment: cumulated locomotor activity

Figure 17A:
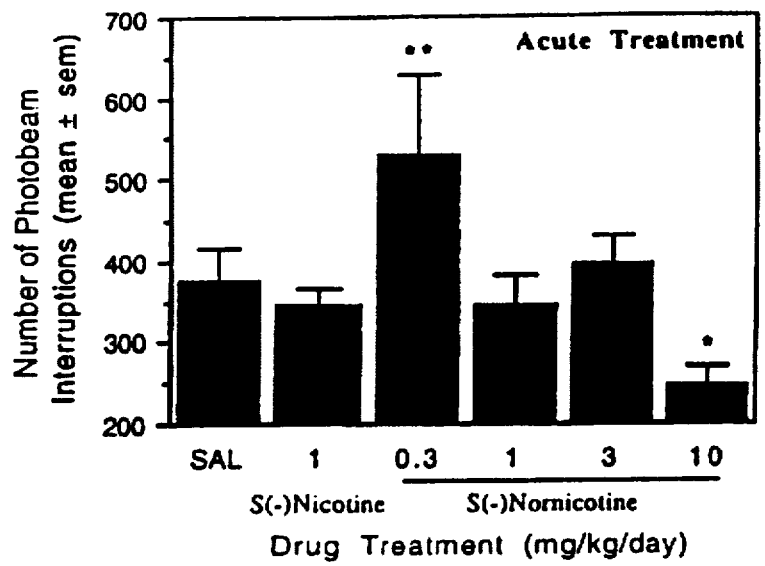
FIG. 17A and 17C show behavioral sensitization and cross-sensitization following repeated administration of S(−) nicotine or S(−) nornicotine.
Figure 17B:
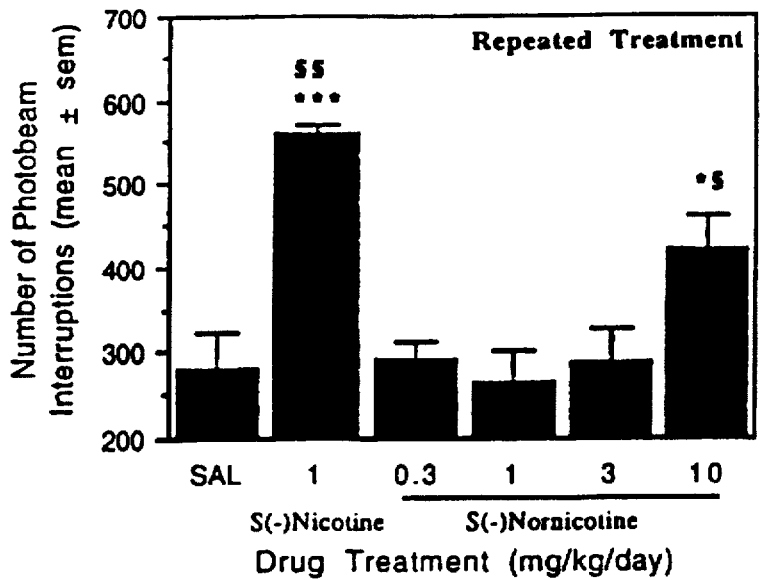
Figure 17C:
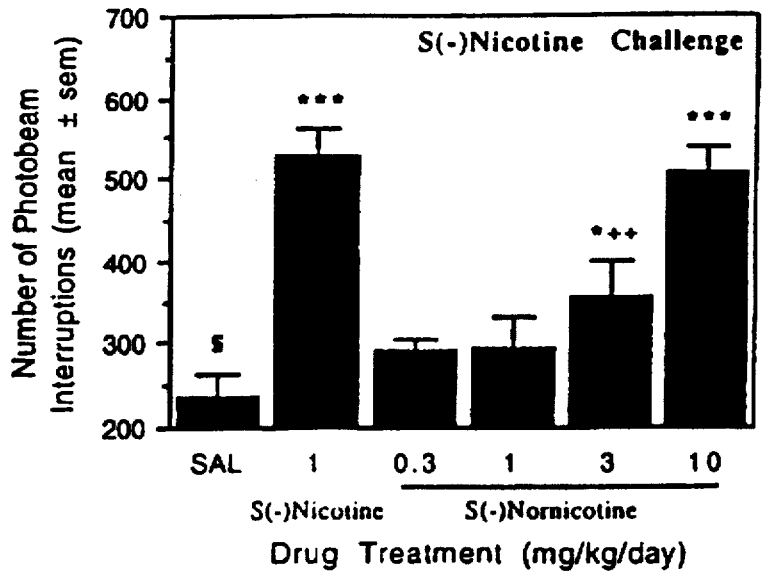

A separate series of experiments was performed to determine the effect of acute and repeated administration of the S(–)enantiomer of nornicotine (0.3–10 mg/kg) on locomotor activity compared to that of S(–) nicotine (1 mg/kg) or saline (FIG. 17). Two-factor ANOVA revealed that the main effect of behavioral session was not significant |F(3,15)=1.09, P>0.05|; however, a significant between-groups treatment factor [F(5,30)=6.73, P<0.001] and a significant treatment× session interaction [F(15,90)=7.26, P<0.0001] were found.

Acute Treatment

Compared to the saline-control group, acute administration of S(–) nicotine (1 mg/kg) did not alter 12 locomotor activity when cumulated over the 50-min session (FIG. 17, top panel). The response to acute S(–) nornicotine was biphasic, depending upon the dose. After acute administration of the low dose (0.3 mg/kg), activity was significantly increased compared to the saline-control group. After administration of 1 and 3 mg/kg, activity was not different from the saline-control group. After the highest dose (10 mg/kg) of S(–) nornicotine, a significant decrease in activity was observed. Thus, stimulation of locomotor activity was observed after acute administration of low doses of S(–) nornicotine, and inhibition was observed after high doses.

Repeated Treatment

Repeated administration of saline did not alter cumulated locomotor activity when compared to acute saline administration (FIG. 17, middle panel). Repeated S(–) nicotine administration significantly increased locomotor activity when compared to either the saline-control group or to the S(–) nicotine group after acute S(–) nicotine administration (FIG. 17, top and middle panel). The increase in activity induced by S(–) nicotine plateaued after the fourth injection.

With repeated administration of S(–) nornicotine, tolerance to the acute stimulatory effect of the low dose (0.3 mg/kg) was observed (FIG. 17, middle panel). Tolerance became apparent following the third injection of the repeated regimen. After each administration of the intermediate doses (1 and 3 mg/kg) of S(–) nornicotine, locomotor activity was not different from that of the saline-control group (FIG. 3., middle panel; and data not shown for 2–7 injections). Tolerance to the acute behavioral depressant effect of the high dose (10 mg/kg) of S(–) nornicotine was also observed, and was evident after the fourth injection of the regimen (data not shown). After the seventh injection of the high dose, activity was significantly increased (364±32 photobeam interruptions) above that of the saline-control group. Following the last administration of the high dose, locomotor activity was stimulated significantly above that of the saline-control group; however, activity was significantly less than that for the group repeatedly administered S(−) nicotine (FIG. 17, middle panel). Thus, similar to S(−) nicotine, behavioral sensitization following repeated administration of the high dose of S(−) nornicotine was observed.

EXAMPLE 15

S(−) Nicotine Challenge

S(−) nicotine challenge decreased activity in the saline-control group, when compared to the same group's activity following acute saline administration (FIG. 17, top and bottom panels). Also, when the group repeatedly administered S(−) nicotine was challenged with S(−) nicotine, activity was significantly increased compared to that of the saline-control group following S(−) nicotine challenge (FIG. 17, bottom panel). Additionally, activity of the S(−) nicotine group following the S(−) nicotine challenge was not different from their activity following the last administration of the repeated regimen of S(−) nicotine (FIG. 17, middle and bottom panels). Thus, behavioral sensitization to repeated S(−) nicotine administration was observed. In contrast, S(−) nicotine challenge had no effect on the groups of rats repeatedly administered the low doses (0.3 and 1.0 mg/kg) of S(−) nornicotine. However, S(−) nicotine challenge significantly stimulated locomotor activity in the groups of rats repeatedly administered 3 and 10 mg/kg S(−) nornicotine, when compared to that of the saline-control group.

Although activity on the last day of repeated administration of the 3 mg/kg group was not different from saline-control group (FIG. 17, middle panel), S(−) nicotine challenge significantly increased activity in the 3 mg/kg group, such that behavioral sensitization was unmasked (FIG. 17, bottom panel). The stimulation of activity observed after S(−) nicotine challenge in the 3 mg/kg group is in sharp contrast to.the S(−) nicotine challenge-induced depression of activity observed in the saline-control group. Furthermore, activity following S(−) nicotine challenge in the 3 mg/kg S(−) nornicotine group was significantly less than that of the S(−) nicotine group after challenge with S(−) nicotine (FIG. 17, bottom panel). With regards to the high dose (10 mg/kg ) S(−) nornicotine group, S(−) nicotine challenge resulted in an increased locomotor activity, which was not significantly different from that observed in this group following their last dose of S(−) nornicotine (FIG. 17, middle panel). Furthermore, the S(−) nicotine challenge-induced increase in activity in the 10 mg/kg S(−) nornicotine group was not different from the activity of the S(−) nicotine group (FIG. 17, bottom panel). Thus, behavioral sensitization was not observed following repeated administration of 3 mg/kg S(−) nornicotine, but upon challenge with S(−) nicotine, sensitization was unmasked. Furthermore, behavioral sensitization was observed following repeated administration of 10 mg/kg S(−) nornicotine, and cross-sensitization was observed following challenge with S(−) nicotine. Thus, the effect of S(−) nicotine challenge was dependent upon the dose of 14 S(−) nornicotine repeatedly administered.

EXAMPLE 16

S(−) nornicotine Experiment: time course

When the time course of the effect of acute and repeated drug administration on locomotor activity was analyzed, the complexity of the response to both S(−) nicotine and S(−) nornicotine was apparent. Three-factor ANOVA revealed significant main effects of treatment [F(5,27)=6.44, P<0.0005] and time (F(4,108)=233.04, P<0.0001], however, the main effect of behavioral session was not significant [F(3,81)=1.38, P>0.05]. Moreover, a significant 3-way interaction [F(60,324)=5.56, P<0.0001] was obtained.

Acute Treatment

Figure 18A:
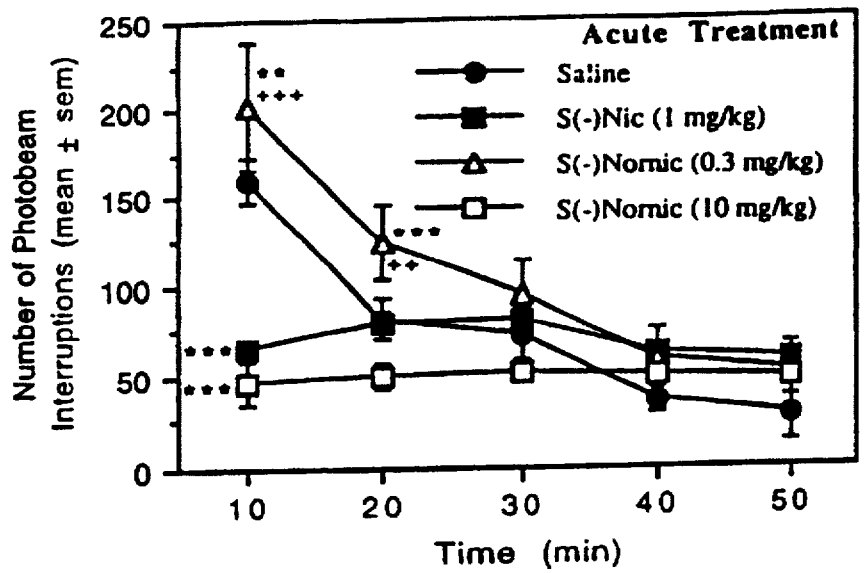
FIG. 18A and 18C show time course of behavioral sessions following acute and repeated administration of S(−) nicotine or S(−) nornicotine and the effect of subsequent challenge with S(−) nicotine.
Figure 18B:
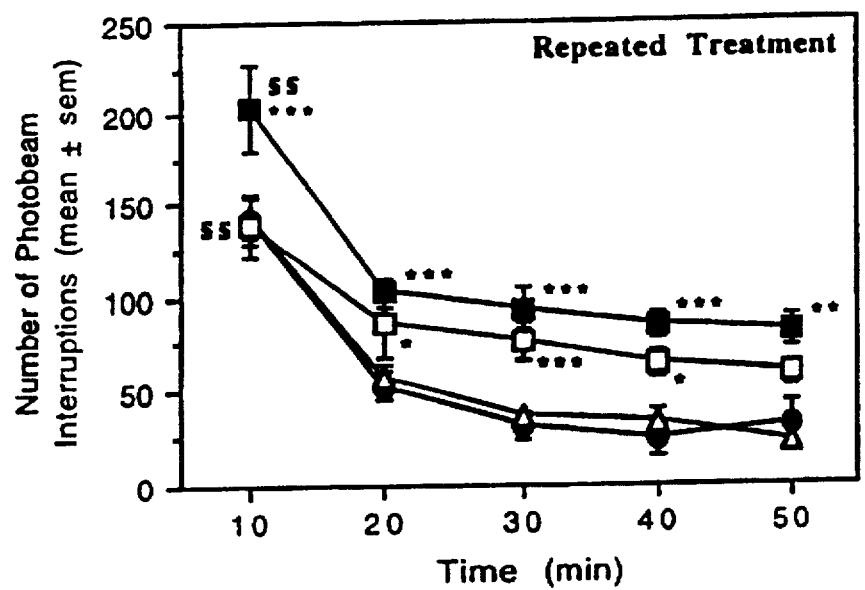
Figure 18C:
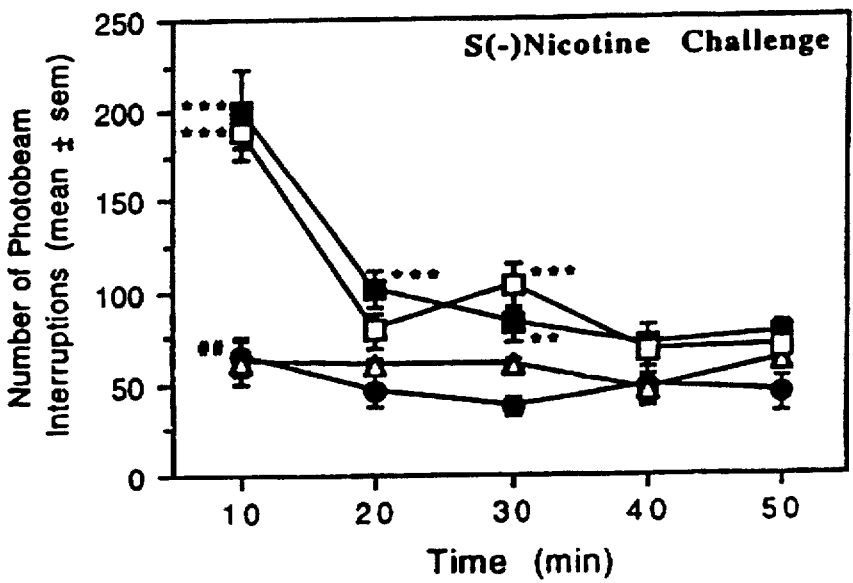

Locomotor activity for the saline-control group decreased over the course of the behavioral session after the acute administration of saline (FIG. 4, top panel). Acute S(−) nicotine administration significantly decreased activity during the first 10 min of the session compared to the saline-control group; but during the remainder of the session, activity was not different from the saline-control group. Compared to the saline-control group, acute administration of 0.3 mg/kg S(−) nornicotine resulted in a significant increase in activity during the first 20 min of the session, and tended to be increased during the remainder of the session (FIG. 18, top panel). The increased activity across the time course of the session after the low dose of S(−) nornicotine resulted in a significant increase in cumulated locomotor activity (FIG. 17, top panel). Thus, in contrast to S(−) nicotine which depressed locomotor activity early in the behavioral session, the low dose of S(−) nornicotine stimulated activity early in the session. Locomotor activity after acute administration of S(−) nornicotine (1 and 3 mg/kg) was not different from the saline-control group over the time course of the session (data not shown), except during the first 10 min of the session when 3 mg/kg produced a significant (P<0.01) decrease in activity (121±14 photobeam interruptions) compared to the saline-control group. Following the high dose (10 mg/kg) of S(−) nornicotine, activity was significantly 15 decreased during the first 10 min of the session; however, during the remainder of the session, it was not different from the saline-control group (FIG. 18, top panel). Thus, the decrease in activity cumulated across the session in response to the high dose (10 mg/kg) of S(−) nornicotine (FIG. 17, top panel) resulted from the initial decrease in activity which was not compensated for by a later increase in activity (FIG. 18, top panel).

Furthermore, at the 10-min time point, activity following 10 mg/kg S(−) nornicotine was significantly (P<0.001) less than that after 3 mg/kg (data not shown). Thus, at the 10-min time point, a dose-related effect of S(−) nornicotine was observed, such that at low doses stimulation of activity occurred, while at high doses depression of activity was apparent.

Repeated Treatment

The saline-control group's locomotor activity decreased across the time course of the session (FIG. 18, middle panel) Repeated administration of S(−) nicotine resulted in a significant increase in activity across the session. Tolerance developed to the decrease in locomotor activity observed during the first 10 min of the session following acute S(−) nicotine adminis-tration. The increase in activity after repeated S(−) nicotine was significantly greater than that of the saline-control group. Following repeated administra-tion of S(−) nornicotine (0.3–3 mg/kg), locomotor activity was not different from the saline-control group, except that during the first 10 min of the session after the 3 mg/kg, a significant (P<0.01) decrease in activity (101±12 photobeam interruptions) was observed (data not shown). Thus, tolerance did not develop to the depressant effect of the 3 mg/kg dose (i.e., no difference was found between the response after acute and repeated administration of this dose at the 10-min time point). Following repeated administration of the high dose (10 mg/kg) of S(−) nornicotine, activity was greater than that of the salinecontrol group during the majority of the time course (FIG. 18, middle panel). From 20–40 min, activity of the 10 mg/kg group was significantly greater than that of the saline-control group; however, at the 10- and 50-min time points, activity was not different from that of the saline-control group. Furthermore, at the 10-min time point, activity was greater after repeated administration of 10 mg/kg S(−) nornicotine than that after its acute administration (FIG. 18, top and middle panels). Thus, following repeated administration of the high dose of S(−) nornicotine, tolerance developed to its depressant effect early in the session, and 16 sensitization was observed to develop later in the session (FIG. 18, middle panel).

EXAMPLE 17
S(−) nicotine Challenge

Following S(−) nicotine challenge, the saline-control group's activity at the first 10-min time point was significantly less than that at the same time point on the last day of the repeated regimen (FIG. 18, middle and bottom panels). During the first 30 min of the session, activity of the S(−) nicotine group was significantly greater than that of the saline-control group challenged with S(−) nicotine (FIG. 18, bottom panel). Later in the session, the activity of the S(−) nicotine group tended to be greater than the saline-control group, however, this was not significant. The effect of S(−) nicotine challenge in the groups repeatedly administered S(−) nornicotine depended upon the dose of S(−) nornicotine administered. Following S(−) nicotine challenge, the activity of the groups repeatedly administered low doses (0.3 and 1 mg/kg) of S(−) nornicotine were not different from that of the saline-control group. During the first 10 min following S(−) nicotine challenge, the locomotor activity of the 3 mg/kg group was significantly ($P<0.001$) increased (134±21 photobeam interruptions) compared to the saline-control group; whereas during this time point on the last day of the repeated regimen, activity of this group was significantly ($P<0.01$) decreased (101±12 photobeam interruptions) compared to the saline-control group (data not shown). Furthermore, direct comparison of activity at the 10-min time point revealed that S(−) nicotine challenge significantly ($P<0.05$) increased activity in the 3 mg/kg group above that on the last day of repeated regimen. For the remainder of the session, activity for this group was not different from the saline-control group challenged with S(−) nicotine. Thus, tolerance did not develop to the depressant effect of 3 mg/kg S(−) nornicotine; however, upon S(−) nicotine challenge, activity of this group was significantly stimulated and behavioral sensitization was unmasked when compared to the saline-control group. Also, during the 10-min and 30-min time points following S(−) nicotine challenge, activity was stimulated significantly in the group repeatedly administered 10 mg/kg S(−) nornicotine.

Furthermore, the activity at the 10-min time point for the 10 mg/kg group was significantly ($P<0.001$) greater than for the 3 mg/kg group. Thus, the amount of S(−) nicotineinduced stimulation of activity was directly related to the dose of S(−) nornicotine repeatedly administered.

EXAMPLE 18
Effect of Conditioning

To determine if the increase in locomotor activity was due at least in part to a conditioned effect of repeated drug administration, all treatment groups were challenged with a saline injection 48 hrs following the S(−) nicotine challenge, and locomotor activity was determined immediately thereafter. The results shown in Table 2 illustrates that locomotor activity for all the drug treatment groups was not different from the saline control group. Thus, a conditioned response to repeated drug administration did not contribute to the observed behavioral sensitization either following repeated S(−) nicotine, R(+) nornicotine or S(−) nornicotine administration, or following S(−) nicotine challenge of any of the groups.

The present study demonstrates that S(−) nornicotine produces behavioral sensitization following repeated administration, whereas R(+) nornicotine does not. Although, following chronic administration, R(+) nornicotine did not produce an overt behavioral effect, R(+) nornicotine enabled an enhanced response to nicotine challenge, such that the rats behaved as though they had been administered S(−) nicotine. The behavioral response to S(−) nicotine and both enantiomers of nornicotine was notably complex.

Following acute injection of nicotine, there was a transient (lasting 10 min) hypoactivity followed by hyperactivity late in the session, when the data were compared to the saline-injected group. When activity was collapsed across time, activity in the acute nicotine group was not different from the saline group. However, following repeated nicotine administration, only hyperactivity was observed across the time course of the session (i.e., tolerance to the hypoactive phase, and sensitization to the hyperactive phase of the behavioral response were observed). The present results are in good agreement with the work of many others studying the effects of nicotine (Stolerman et al., 1973, 1974; Clarke and Kumar, 1983; Ksir et al., 1985, 1987; Collins et al., 1988, 1990; Clarke et al., 1988; Fung and Lau, 1988; Schoaib and Stolerman, 1992; Benwell and Balfour, 1992; Ksir, 1994; Stolerman et al., 1995).

Interestingly, after both acute and chronic administration, an enantioselective effect of norNIC on activity was observed in the present study. Acute administration of the low dose of Sl-) nornicotine produced an early (lasting 20 min) hyperactive phase, in contrast to S(−) nicotine; and when the data were collapsed across the session, an increased activity was observed compared to saline controls. However, the high dose of S(−) nornicotine produced an early (lasting 10 min) hypoactivity similar to S(−) nicotine, and the cumulated results also indicated significant hypoactivity. In contrast, activity following acute administration of the low dose of R(+) nornicotine was not different from saline; whereas, the high dose resulted in early (lasting 20 min) hypoactivity, which in contrast to S(−) nicotine did not rebound later in the session. The present behavioral results are in agreement with the findings of Stolerman et al. (1995) who recently reported that acute R(+) nornicotine decreased locomotor activity in rats. Thus, acute R(+) nornicotine administration resulted in an inverted-U shaped dose response curve in the present study.

Following chronic administration of S(−) nornicotine, behavioral sensitization was observed, similar to S(−) nicotine; and when this group was challenged with S(−) nicotine 48 hrs following the last dose of S(−) nornicotine, crosssensitization was observed (i.e., activity after S(−) nicotine challenge was not different from activity on the last day of repeated administration), suggesting that a similar mechanism may be involved. Moreover, the time course of activity and the cumulated response reveal that repeated administration of the high dose of R(+) nornicotine resulted in activity not different from the saline-control group (i.e., tolerance developed to the depressant effect after acute administration), whereas activity was still depressed after chronic administration of the lowest dose of R(+) nornicotine. It is important to note that the S(−) nicotine group (the positive control) was sensitized following repeated S(−) nicotine injection in this study. Surprisingly, when the R(+)

nornicotine group was challenged with S(−) nicotine, the rats responded as if they had received chronic nicotine. Thus, R(+) nornicotine produced a dose-related sensitization to the stimulatory effect of S(−) nicotine. It is important to note that the activity of the R(+) nornicotine group after S(−) nicotine challenge was significantly greater than the activity of the same group on the last day of repeated R(+) nornicotine treatment. This is the first report of the behavioral effects of chronic administration of S(−) nornicotine or R(+) nornicotine. Stolerman et al. (1995) reported recently that after chronic administration of S(−) nicotine, R(+) nornicotine administration resulted in increased activity (i.e., cross-sensitization). Thus, either when chronic S(−) nicotine (Stolerman et al., 1995) or when chronic S(−) nornicotine (present study) are administered, cross-sensitization is observed, suggesting a common mechanism of action.

EXAMPLE 19

To determine if the increase in activity was due to a conditioned effect of the repeated drug administration, all the treatment groups were challenged with saline 48 hrs following the S(−) nicotine challenge, and activity was determined immediately thereafter. Locomotor activity for all the drug treatment groups was not different from the saline control group. Thus, a conditioned response to the repeated drug administration did not contribute to the observed behavioral sensitization.

Similar to S(−) nicotine, repeated S(−) or R(+) nornicotine administration was capable of activating the neural mechanism(s) responsible for behavioral sensitization, even though R(+) nornicotine produced no overt behavioral effect after its administration. The mechanism of the behavioral effects of S(−) nornicotine and R(+) nornicotine are presently not known. Drugs of abuse have been suggested to produce their locomotor stimulant and reinforcing effects by activating the mesolimbic DA system (Fibiger and Phillips, 1987; Corrigall et al., 1992, 1994; Balfour and Benwell, 1993). Furthermore, destruction of nucleus accumbens DA neurons with 6-hydroxydopamine was reported to reduce the locomotor stimulant and reinforcing effects of S(−) nicotine (Singer et al., 1982; Clarke et al., 1988; Corrigall et al., 1992), and cause a reduction in the number of nicotinic binding sites in nucleus accumbens (Clarke and Pert, 1985), suggesting that a significant portion of the nicotinic receptors are located on DA presynaptic terminals. Thus, the locomotor stimulant and reinforcing effects of nicotine may be due to activation of the mesolimbic DA system. We have reported that S(−) nornicotine evokes a concentration-dependent and Ca+-dependent increase in endogenous DA release from rat striatal slices (Dwoskin et al., 1993). (+) nornicotine was also shown to evoke a concentration-dependent increase in [3H] DA release from mouse striatal synaptosomes (Grady et al., 1992); however it should be noted that racemic-nornicotine was used in this study. More recently, we found that these effects of S(−) nornicotine are inhibited by mecamylamine and DHβE, suggesting a nicotinic receptor-mediated effect (Teng et al., 1996). Thus, S(−) nornicotine may produce its locomotor stimulant effects by activating DA systems, similar to nicotine.

In summary, the results suggest that nornicotine, a nicotine metabolite present in brain following nicotine administration (Crooks et al., 1995, 1996), is pharmacologically active and may contribute to the behavioral and neuropharmacological effects of nicotine.

TABLE 2

The increase in locomotor activity following repeated S(−) nicotine:
R(+) or S(−) nornicotine are not conditioned responses
Treatment Group a Locomotor activity
(number of photobeam interruptions/50 min session)

|  | R(+) experiment | S(−) experiment |
|---|---|---|
| Saline | 424 ± 17 | 350 ± 43 |
| S(−) nicotine (1 mg/kg) | 485 ± 41 | 429 ± 34 |
| nornicotine (0.3 mg/kg) | 368 ± 39 | 352 ± 17 |
| nornicotine (1.0 mg/kg) | 478 ± 40 | 333 ± 38 |
| nornicotine (3.0 mg/kg) | 498 ± 44 | 394 ± 50 |
| nornicotine (10 mg/kg) | 234 ± 30 | 459 ± 26 |

N = 6/group
data are expressed as cumulated locomotor activity during a 50-min behavioral session immediately following a saline injection (s.c.) which occurred 48 hrs following S(−) nicotine challenge.

EXAMPLE 20

Nornicotine Partially Substitutes for Amphetamine in a Drug Discrimination Paradigm in Rats. Rats were trained in on two-lever food-reinforced operant tasks to discriminate amphetamine (1 mg/kg) from saline. After discrimination training stabilized, test doses of amphetamine (0.0625–2.0 mg/kg), nicotine (0.1–1.0 mg/kg) or nornicotine (1–10 mg/kg) were assessed for their ability to substitute for the amphetamine training dose during brief test sessions in which food reinforcement was withheld. As expected, as the test dose of amphetamine increased, there was a dose-related increase in amphetamine-appropriate responding, with both 1 and 2 mg/kg test doses substituting fully for the amphetamine training dose. Both nicotine and nornicotine showed partial substitution (approximately 50% amphetamine-appropriate responding) for the amphetamine training dose, with nicotine being more potent than nornicotine. Rate suppressant effects prevented the assessment higher doses of nicotine or nornicotine. Thus, while nicotine and nornicotine share similar discriminative stimulus properties, the mechanism that mediates this effect appears to differ, at least in part, from that activated by amphetamine.

Similar to other types of stimulant drugs such as amphetamine, evidence indicates that dopaminergic systems in the brain mediate, at least in part, the ability of nicotine to produce reinforcement (7,8,24), locomotor sensitization (5), and a discriminative stimulus effect (6,19,23). Since both nicotine and amphetamine release dopamine (10), this common action may explain why these drugs produce discriminative stimulus effects that partially substitute for each other (4,15,26). However, full substitution between nicotine and amphetamine discriminative stimulus effects is generally not obtained, probably because the discriminative stimulus effect of nicotine, in contrast to amphetamine, involves a significant cholinergic component (15,27).

In addition to nicotine, other alkaloids in tobacco may contribute to the behavioral effects of smoking tobacco. Nornicotine is an alkaloid in tobacco that is detectable in the urine of human smokers (30). In addition to being a constituent of tobacco, nornicotine is a minor nicotine metabolite formed from the N-demethylation of nicotine (1). When rats are injected peripherally with nicotine, significant levels of nornicotine are detected in brain four hours later (9).

Evidence suggests that nornicotine may have behavioral effects similar to other stimulant drugs. For example, in one study using dogs, both nicotine and nornicotine altered responding under two different food-maintained operant schedules in a manner similar to cocaine (22). More recently, repeated treatments with either nicotine or nornicotine have been shown to produce behavioral sensitization (11,25). In these studies, nornicotine was less potent than nicotine.

Other than its effects on operant responding and locomotor activity, however, it is unclear if nornicotine produces either discriminative stimulus or reinforcing effects like other stimulants. The present study, therefore, used a drug discrimination paradigm in rats to examine the ability of nornicotine to substitute for amphetamine, thus providing evidence for shared discriminative stimulus properties.

EXAMPLE 21
Animals

Nine male Sprague-Hawley rats were obtained from Harlan Industries (Indianapolis, Ind.) and were caged individually with water continuously available. Food access was restricted in order to maintain body weights at approximately 80% of free-feeding weight. Prior to the start of the experiment, all rats received a single injection of amphetamine (1 mg.kg, IP) as part of an unrelated experiment. Apparatus Six operant chambers (ENV-001, Med Associates, St. Albans, Vt.) enclosed in a sound attenuating environment were used. Located in the bottom center of the front panel in each chamber was a 5×4.-cm opening to a recessed food tray. Two metal response levers were located on the front panel, one on each side of the food tray. The center of each lever was mounted 7.3 cm from the grid floor. A 28-Vcue light, 3 cm in diameter, was centered 6 cm above each lever. A personal computer, interfaced to the chamber with Med Associates equipment, controlled the experimental sessions and collected data.

Amphetamine discrimination training.

The general procedures utilized to establish amphetamine discrimination were similar to those outlined previously (13). Briefly, rats were first given access to food pellets (45 mg sucrose pellet, Noyes Co., Lancaster, N.H.) dispensed noncontingently into the food tray with both levers present. One lever was then removed and the rat was shaped to depress the other lever for food reinforcement. Following this, rats received 15-min daily sessions in which the lever (left or right) available for food reinforcement was alternated daily. Across these daily sessions, the fixed ratio (FR) requirement to obtain food was gradually increased from an FR1 to an FR25. The start of each session was signaled by the onset of both cue lights mounted above the levers, and the termination of each session was signaled by the offset of these lights. This training phase was continued until the rat earned 20 reinforces on an FR25 schedule for two days.

Amphetamine discrimination training was conducted Monday through Friday. For this training, both levers were mounted in the chamber. Amphetamine (A; 1 mg/kg) or saline (S), was injected IP 15 min prior to the start of the session, with the order of injections being either AASS or SSAA. The left lever was designated as the amphetamine-correct lever for 4 rats, while the right lever was amphetamine -correct for 5 rats. On Monday, Wednesday and Friday, injection-appropriate responding was food-reinforced on an FR25 schedule for the entire 15-min session. However, 2-min extinction periods were instituted at the beginning of sessions on Tuesday and Thursday (one amphetamine and one saline test per week) to assess the control of amphetamine (or saline) over responding. During this brief extinction period, the distribution of responding was monitored, but lever pressing did not result in food reinforcement. During the remaining 13 min of these sessions, contingent reinforcement for injection-appropriate responding was reinstated. This phase of training was continued until the rat completed the first FR25 on the correct lever for 10 consecutive sessions and also completed 80% or more responses on the injection-appropriate lever during 4 consecutive extinction periods.

EXAMPLE 22
Amphetamine, nicotine and nornicotine substitution tests

The substitution phase was identical to the previously described amphetamine discrimination phase, except for the Friday session, which was decreased to a 4-min extinction session with no food available. This session was used to assess the ability of amphetamine (0.0625, 0.125, 0.25, 0.5, 1.0 or 2.0 mg/kg), nicotine (0, 0.1, 0.3, 1.0 or 3.0 mg/kg) and nornicotine (0, 1, 3 or 10 mg/kg) to substitute for the amphetamine training dose. Each dose was administered to two different Friday sessions according to a randomized block design. Rats were first tested with all amphetamine doses (2 determination per dose) give IP 15 min prior to the session. Subsequently, rats were tested with all nicotine doses (2 determinations per dose), followed by all nornicotine doses (1–3 determinations per dose). Nicotine and nornicotine test doses were given either 15 min (4 rats) or 45 min (5 rats) prior to the beginning of the session. For each determination of amphetamine-appropriate responding, rats were required to perform 15 or more responses during the 4-min extinction session.

In all cases, substitution testing was conducted only if the rat responded with 80% or better injection-appropriate responding during the 2-min extinction periods on Tuesday and Thursday prior to the respective Friday session. Rats that did not meet this criterion remained in the home cage on Friday and were fed their daily allotment of food.

Drugs d-Amphetamine sulfate and S(−) nicotine bitartrate were purchased from Sigma Chemical Co. (St. Louis Mo.) and Research Biochemicals Inc. (Natick, Mass.), respectively. S(−) Nornicotine diperchlorate was synthesized according to unpublished methods (Crooks, et al., unpublished). All drugs were dissolved in saline and injected IP in a volume of 1 ml/kg. Dosages were based on the salt form of each drug.

Figure 14A:
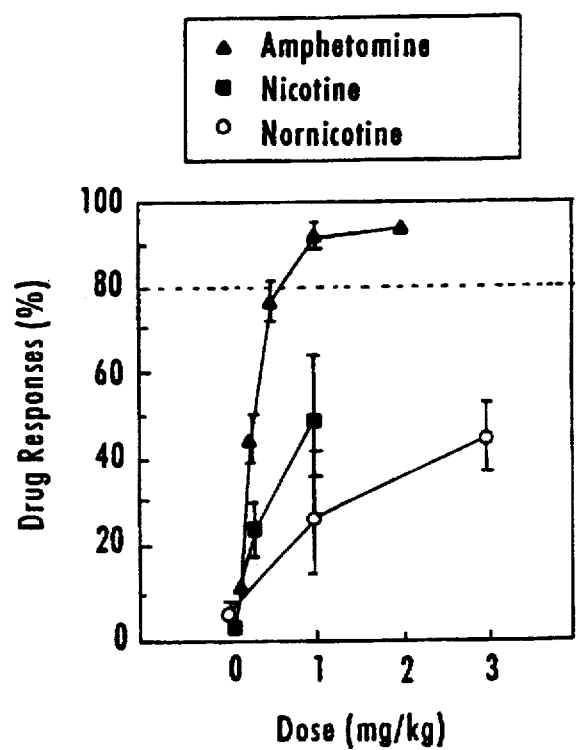
FIG. 14A and 14B show mean percent of amphetamine-appropriate responses (top figure) and total responses (bottom figure) when nicotine or nornicotine were administered 45 min prior to the substitution test session.
Figure 14B:
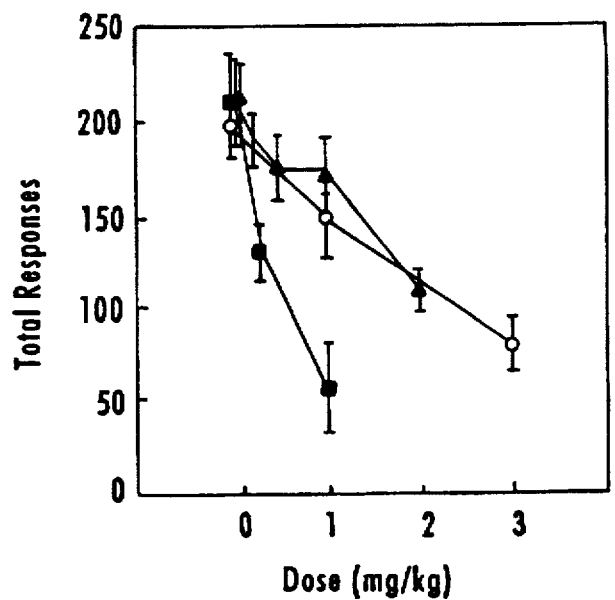

FIG. 14 illustrates the dose-effect curves for percent amphetamine-appropriate lever pressing and total number of lever presses when amphetamine, nicotine or nornicotine was given 15 min prior to the substitution test session. As expected, as the test dose of amphetamine increased, a graded increase in amphetamine-appropriate lever pressing was observed. The highest doses (1 and 2 mg/kg) of amphetamine tested produced greater than 80% amphetamine-appropriate responding, indicating that these doses substituted fully for the amphetamine training dose (1 mg/kg). A significant amphetamine dose-related decrease in total number of lever presses was observed during the substitution test session.

As shown in FIG. 14, dose-related increases in amphetamines appropriate lever pressing were also evident during substitution tests with nicotine and nornicotine. Approximately 50% amphetamine-appropriate responding was engendered by nicotine (1 mg/kg) and nornicotine (3 mg.kg), indicating partial substitution. Across the dose ranges examined, significant decreases in total number of lever presses on substitution tests with nicotine and nornicotine were observed. At higher doses of nicotine and nornicotine, rats failed to meet the criterion of 15 or more responses during the 4-min extinction session, thus precluding determination of percent amphetamine-appropriate responding.

Figure 15A:
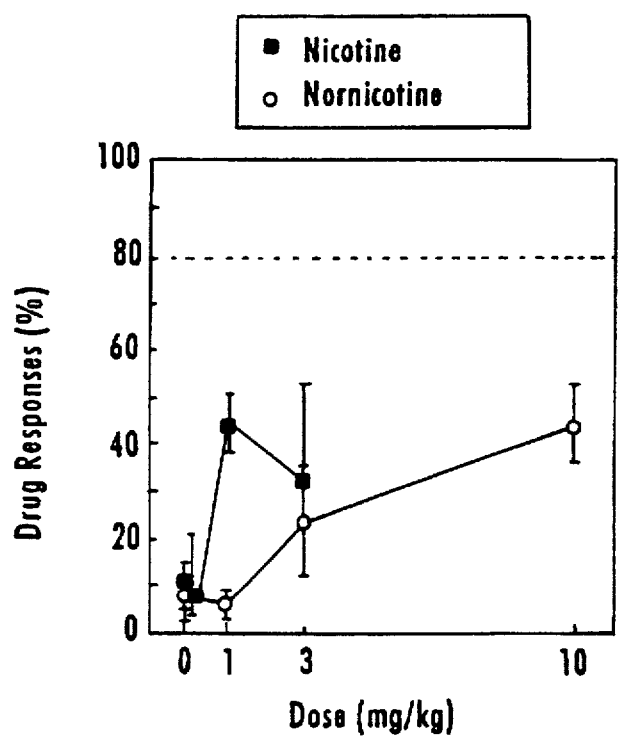
FIG. 15A and 15B show time course of behavioral sessions following acute and repeated administration of S(−) nicotine or R(+)nornicotine and the effect of subsequent challenge with S(−)nicotine.
Figure 15B:
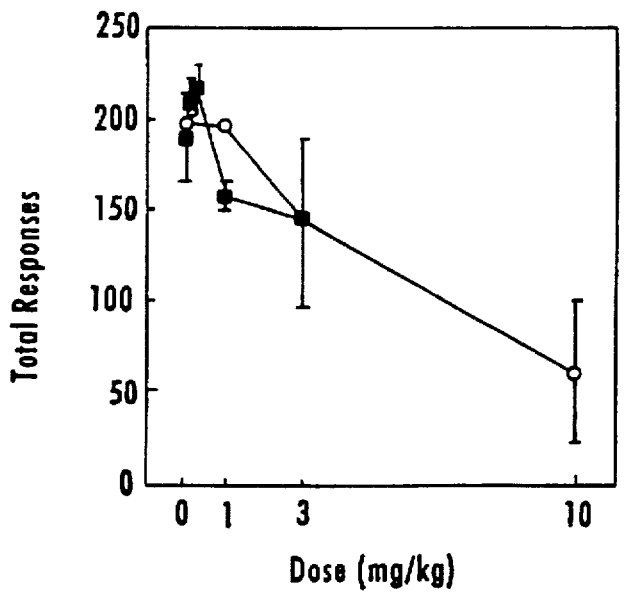

To reduce the rate suppressant effects of nicotine and nornicotine, the same dose ranges were tested at 45 min prior to the substitution session (see FIG. 15). Similar to the results obtained after 15 min, dose-related increases in amphetamine-appropriate lever pressing were evident on substitution sessions after administration of nicotine or nornicotine.

The maximum amount of amphetamine-appropriate responding evident with nicotine and nornicotine was 1 and 10 mg/kg, respectively. These doses engendered approximately 50% amphetamine-appropriate responding, indicating partial substitution was obtained again. Examination of data from individual rats revealed that none of the rats reached 80% amphetamine-correct responding with any of the doses of either nicotine or nornicotine. Amphetamine-correct responses for individual rats ranged from 31–59i for nicotine (1 mg/kg) and 33–61% for nornicotine (10 mg/kg). A significant decrease in total number of lever presses was also observed on substitution tests with nicotine and nornicotine.

Previous work has shown that nornicotine substitutes fully for nicotine in a drug discrimination paradigm in rats (14). The present study demonstrates that nornicotine also has a behavioral profile similar to nicotine when tested for its ability to substitute for amphetamine as a discriminative stimulus. Since both nicotine and nornicotine partially substituted for amphetamine in the drug discrimination paradigm, both of these drugs may possess, at least to some extent, amphetamine-like stimulus effects.

Although nornicotine was less potent than nicotine in its ability to partially substitute for amphetamine, nornicotine had a similar efficacy compared to nicotine. The observed difference in potency is in good agreement with other studies comparing nicotine and nornicotine effects on locomotor activity and schedule-controlled operant responding (11,21, 22).

With regard to drug discrimination studies in general, there are several explanations to explain why a test drug produces partial, rather than full, substitution for the training drug. For example, evidence for partial substitution may reflect an averaging artifact that occurs when group data do not adequately represent individual data. That is, if some individual rats at a particular dose shown full substitution (better than 80% drug-appropriate responding), whereas other rats show no substitution (less than 20% drug-appropriate responding), combining the data would yield a group average indicative of partial substitution (approximately 50% drug-appropriate responding). However, examination of data from individual rats in the present study revealed that all individuals showed full substitution with amphetamine, whereas all individuals showed partial substitution with nicotine and nornicotine across the dose range examined. Thus, in the present experiment, the group data were representative of the effect observed among individuals.

For drug discrimination studies in general, another explanation for obtaining a partial substitution is that rate suppressant effects may prevent the expression of full substitution. In the present study, both nicotine and nornicotine had clear rate suppressant effects. At 15 min after injection, the rate suppressant effects precluded the assessment of amphetamine-appropriate responding at the highest doses of nicotine and nornicotine tested. At 45 min after injection, however, response rate was sufficient to define amphetamine-appropriate responding across all doses of nicotine and nornicotine tested. At the longer injection-test interval, a plateau in the dose-effect curves were reached at 50' amphetamine-appropriate responding. Thus, an explanation other than nonspecific rate suppression likely accounts for the partial substitution obtained with nicotine and nornicotine.

The explanation for the partial substitution evident in the present study is that the mechanisms that underlie the discriminative stimulus effects of nicotine and nornicotine do not overlap completely with the mechanisms that underlie the discriminative stimulus effects of amphetamine. Evidence indicates that enhanced dopamine release is responsible, at least in part, for the discriminative stimulus effects of amphetamine (2,28) and nicotine (6,19,23). However, differential effects of these drugs at dopaminergic somatodendritic (ventral tegmental area) and terminal (nucleus accumbens) brain regions may underlie the differential discriminative stimulus properties obtained. That is, while amphetamine displaces dopamine directly at the presynaptic terminal, nicotine-induced dopamine release is regulated by nicotinic receptors in the ventral tegmental area (18). Concomitant with this neurochemical dissociation, amphetamine-induced locomotor behavior involves primarily the nucleus accumbens, whereas nicotine seems to increase locomotor behavior primarily via an action in the ventral tegmental area (17,20).

Further, although both amphetamine and nicotine produce locomotor sensitization with repeated treatments, cross-sensitization between nicotine and amphetamine has not been observed (29), suggesting different mechanisms of action. Perhaps differential actions on dopaminergic systems are responsible for the failure of either nicotine or nornicotine to substitution fully for amphetamine in the present report.

Alternatively, the differential actions of amphetamine, nicotine and nornicotine on nondopaminergic systems may explain the partial substitution obtained in the present report. In particular, in contrast to amphetamine, nicotine and nornicotine discriminative stimulus effects involve a significant cholinergic component (15,27), an effect that may not be directly tied to any dopaminergic system. For example, nicotinic receptors located in the pedunculopontine tegmental nucleus, which are thought to be involved in nicotine reward (16), may be involved. In addition to cholinergic receptors, nicotine reward is blocked by 5-HT3 receptor antagonists, whereas amphetamine reward is not (3). Further, while $H_1$ antagonists substitute fully for amphetamine in a drug discrimination paradigm (12), histamine receptors may not be involved in the discriminative stimulus effect of nicotine. Thus, differential activation of these nondopaminergic systems, or some other system, may interfere with the ability of nicotine and nornicotine to produce a dopamine-mediated discriminative stimulus similar to that produced by amphetamine.

EXAMPLE 23

The methods of treating dopamine related conditions and disease states comprise administering an effective amount of a composition comprising a compound selected from the group consisting of S-(−) nornicotine or R-(+) nornicotine, free base forms, inorganic acid salts and organic acid salt forms thereof. Consistent with the invention the dopamine related conditions and/or disease states may be selected from, but not limited to myasthenia gravis, Parkinson's disease, Alzheimer's disease, schizophrenia, eating disorders, drug addiction and use as a substitute for psychostimulant self-administration. Pharmaceutical formulations for the treatment of these conditions are set forth below.

The compounds and compositions of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. Topical application can be in the form of ointments, creams, lotions, jellies, sprays, douches, and the like. For oral administration either solid or fluid unit dosage forms can be prepared with the compounds of the invention. The compounds are useful in pharmaceutical compositions (wt %) of the active ingredient with a carrier or vehicle in the composition in about 1 to 20% and preferably about 5 to 15%.

Either fluid or solid unit dosage forms can be readily prepared for oral administration. For example, the compounds of the invention I can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixers may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharine or a biological sweetener and a flavoring agent in the form of an elixer.

Pharmaceutical compositions for parenteral and suppository administration can also be obtained using techniques standard in the art. The above parenteral solutions or suspensions may be administered transdermally and, if desired a more concentrated slow release form may be administered. Accordingly, incorporation of the active compounds in a slow release matrix may be implemented for administering transdermally. The compounds may be administered transdermally at about 1 to 20% of the composition and preferably about 5 to 15% wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of the blood-concentration versus time profile, increased patient compliance due to elimination of multiple dosing schedules, bypassing the hepatic "first-pass" metabolism, avoiding gastrointestinal incompatibilities and providing a predictable and extended duration of activity. However, the main function of the skin is to act as a barrier to entering compounds. As a consequence, transdermal therapy has so far been restricted to a limited number of drugs that possess the desirable physiochemical properties for diffusion across the skin barrier. One effective method of overcoming the barrier function of the skin is to include a penetration enhancer in the formulation of a transdermal therapeutic system. See Barry, Brian W.: *Dermatological Formulations: Percutaneous Absorption* (Dekker, New York, 1983); Bronough et al, *Percutaneous Absorption, Mechanisms-Methodology-Drug Delivery*, (Marcel Dekker, New York, N.Y. 1985); and Monkhouse et al, Transdermal drug deliver-problems and promises. *Drug Dev. Ind. Pharm.*, 14, 183–209 (1988).

A penetration enhancer is a chemical compound that, when included in a formulation, temporarily increases the permeability of the skin to a drug allowing more of the drug to be absorbed in a shorter period of time. Several different types of penetration enhancers have been reported such as dimethylsulfoxide, n-decyl methyl sulfoxide, N,N-dimethylacetamide, N<Ni-dimethylformamide, 1-dodecylazacycloheptan-2-one (Azone), propylene glycol, ethanol, pyrrolidones such as N-methyl-2-pyrrrolidone (NMP) and surfactants. See Bronough et al, supra, and Stoughton et al, Azone: a New Non-toxic enhancer of percutaneous penetration. *Drug Dev. Inc. Pharm.*, 9, 725–744 (1983).

N-methyl-2-pyrrolidone is a versatile solvent which is miscible with water, ethyl alcohol, ether, chloroform, benzene, ethyl acetate and carbon disulfide. N-methylpyrrolidone has been widely used as a solvent in industrial processes such as petroleum refining. GAF Corp.: "M-Pyrol (N-methyl-2-pyrrolidone) Handbook.". GAF Corp., New YorK, 1972. It is currently used as a solubilizing agent in topical and parenteral veterinary pharmaceuticals and is now under consideration for use in products intended for humans, Wells, D. A. et al: Disposition and Metabolism of Double-Labeled [$^3$H and $^{14}$C] N-methyl-2-pyrrolidone in the Rat. *Drug Met. Disps.*, 16, 243–249 (1988). Animal and human experiments have shown very little irritation or sensitization potential. Ames type assays and chronic exposure studies have not revealed any significant toxicity, Wells et al, Mutagenicity and Cytotoxicity of N-methyl-2-p [yrrolidone and 4-(methyl amino) Butanoic Acid in the Salmonella/microsome Assay. *J. Appl. Tox.*, 8, 135–139 (1988). N-methylpyrrolidone has also been shown to be an effective penetration enhancer. Barry et al, Optimization and Bioavailability of Topical Steroids: Penetration Enhancers Under Occlusion. *J. Inv. Derm.*, 82, 49–52 (1984); Akter et al, Absorption Through human Skin of Ibuprofen and Flurbiprofen; Effect of Dose Variation, Deposited Drug Films, Occlusion and the Penetration Enhancer N-methyl-2-pyrrolidone. *J. Pharm. Pharmacol.*, 37, 27–37 (1984); Holegaard et al, Vesical Effect on Topical Drug Delivery IV. Effect of N-methylpyrrolidone and Polar Lipids on Percutaneous Transport. *Int. J. Pharm.*, 43, 233–240 (1988); Sugibayashi et al, Effect of Several Penetration Enhancers on the Percutaneous Absorption of Indomethacin in Hairless Rat. *Chem. Pharm. Bull.*, 36, 1519–1529 (1988); Bennett et al, Optimization of Bioavailability of Topical Steroids: Non-occluded penetration Enhancers Under Thermodynamic Control. *J. Pharm. Pharmacol.*, 37, 298–304 (1985); Sasaki et al, Enhancing Effect of Pyrrolidone Derivatives on Transderman Drug Delivery. 1. *Ing. J. Pharm.*, 44, 14–24 (1988); lee et al, Toxicity of N-methyl-2-pyrrolidone (NMP): Tetratogenic, Subchronic and Two-year Inhalation Studies, *Fund. Appl., Tox.*, 9, 222–235 (1987).

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a compound according to the present invention is about 10 to 500 mg when administered by either oral or rectal dose from 1 to 3 times daily. This is about 0.2 to about 35 mg per kilogram of the subject's weight administered per day. Preferably about 20 to about 175 mg are administered orally or rectally 1 to 3 times a day for an adult human. The required dose is considerably less when administered parenterally, preferably about 10 to about 60 mg may be administered intramuscularly or transdermally, 1 or 2 times a day for an adult human.

Compounds of the present invention may be administered topically at about 1 to 20 wto of the composition, and preferably about 5 to 15 wt %. Other formulations and dosing known in the art as set forth in Remingtons Pharmaceutical Sciences, 18th Ed. Mack Publishing Co. (1990) is incorporated herein by reference in its entirety.

DETAILED DESCRIPTION OF DRAWINGS

FIG. 1 summarizes the current understanding of the origin of NIC metabolites present in brain after peripheral NIC administration, and is primarily based on our ongoing studies (Crooks et al., 1995b, 1996, AP 7.5).

FIG. 2. shows the time course of appearance of NIC and COT in brain from representative rats NIC distribution to brain is rapid, maximum uptake occurring between 30–60 min. Also, NIC efflux out of brain is relatively rapid, since only low levels were detected in CNS at 4hrs post-NIC-injection. COT accumulated in brain much more slowly than NIC, and was still detectable at 18 hrs post-injection. Thus, NIC is distributed to brain quickly, whereas COT is distributed to brain more slowly and has a longer residence time in the CNS than NIC. A second "metabolite" (Peak A, FIG. 2) was also detected at each time point and most likely results from a combination of metabolic cleavage of the N-methyl group and dissociated-[$^3$H], i e, Peak A represents an oxidized 1-carbon unit and indicates the extent of NIC N-demethylation. Note, in our subsequent studies with [2'-$^{14}$C]NIC, Peak A was not observed, which is consistent with our interpretation of the results (Table 1). The long residence time of Peak A in the CNS suggests that the [$^3$H] associated with this peal; may be present as covalently bound [$^3$H], perhaps to protein or other macromolecular structures Of note is the observation that maximum metabolite appearance in the CNS occurred at 4 hr post-NIC injection.

FIG. 3 shows NIC and four NIC metabolites have recently been detected in rat brain 4 hr after s.c. injection of [2'-$^{14}$C]NIC.

FIG. 4. In a concentration-dependent manner, NIC (left) and norNIC (right)-evoke an increase in [$^3$H]overflow from [$^3$H]DA-preloaded rat striatal slices, but fail to produce a plateau in response. Insets illustrate the response to the low concentration range. Time-courses of 0.1–100 µM NIC and norNIC are illustrated in lower panels NIC or norNIC were added to the superfusion buffer after collection of the second sample (indicated by the arrow) and remained in the buffer for 60 min. N=5–12 and 8 rats for NIC and norNIC, respectively. *P<0.05 different from basal and from control at same point. $P<0.05 different from control at same time point, #P<0.05, ##P<0.005 different from control, Fisher's LSD post hoc test FIG. 5 Time course (top 2 panels) and concentration-dependent NIC-evoked [$^3$H] overflow (bottom panel) from [$^3$H]DA-preloaded rat striatal slices in response to a 2-min exposure. NIC exposure indicated by the bar under time course. Note: 1-min sample collection period. Plateau in [$^3$H] overflow observed at 30 mM (not shown). N=4 rats.

Figure 6:
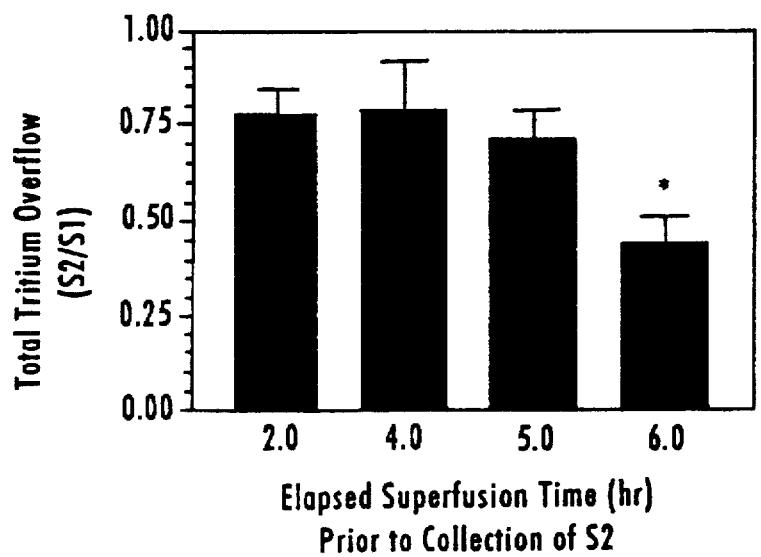
FIG. 6 shows prolonged viability of superfused rat striatal slices. Total [$^3$H]overflow in response to S2 (electrical-field stimulation; 60 pulses, 1 Hz) as a function of elapsed time (hrs) since S1, illustrating that slices are viable for 5 hrs. *P<0.05, Fisher's LSD post hoc test. N=4–6 rats.

FIG. 6 shows prolonged viability of superfused rat striatal slices. Total [$^3$H] overflow in response to S2 (electrical-field stimulation; 60 pulses, 1 Hz) as a function of elapsed time (hrs) since Si, illustrating that slices are viable for 5 hrs. *P<0.05, Fisher's LSD post hoc test. N=4–6 rats.

FIG. 7 NIC (10 µM)-evoked [3H]overflow is in physiologically relevant response range. Rat striatal slices were depolarized with 10 µM NIC, 20 mM K+or 1 Hz, 60 pulses or 3 Hz, 180 pulses electrical field stimulation. Raclopride (1 µM)was added to the superfusion buffer 20 min prior to electrical stimulation. *P.0.05, paired t-test. N=4.

Figure 8B:
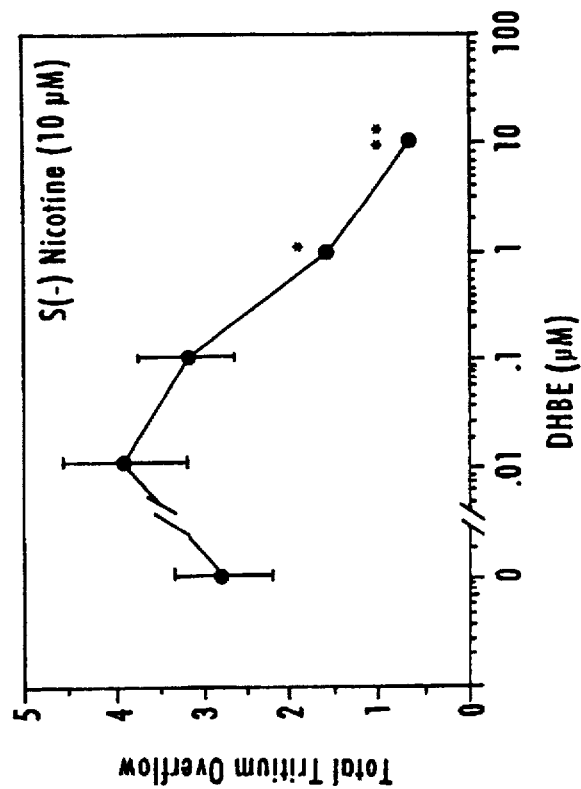
FIG. 8A and 8B show MEC (0.01–100 µM) and DHβE (0.01–10 µM) inhibit NIC (10 µM)-evoked [$^3$H]DA release from rat striatal slices. MEC or DHβE was included in the superfusion buffer for 60 min prior to the addition of NIC, and superfusion continued for 60 min in the presence of NIC+antagonist. Data are presented as Mean±S.E.M. total [$^3$H]overflow for N=8 rats for MEC, and N=5 for DHβE. *P<0.05, **P<0.005 different from MC-control, Fisher's LSD post hoc test.
Figure 8A:
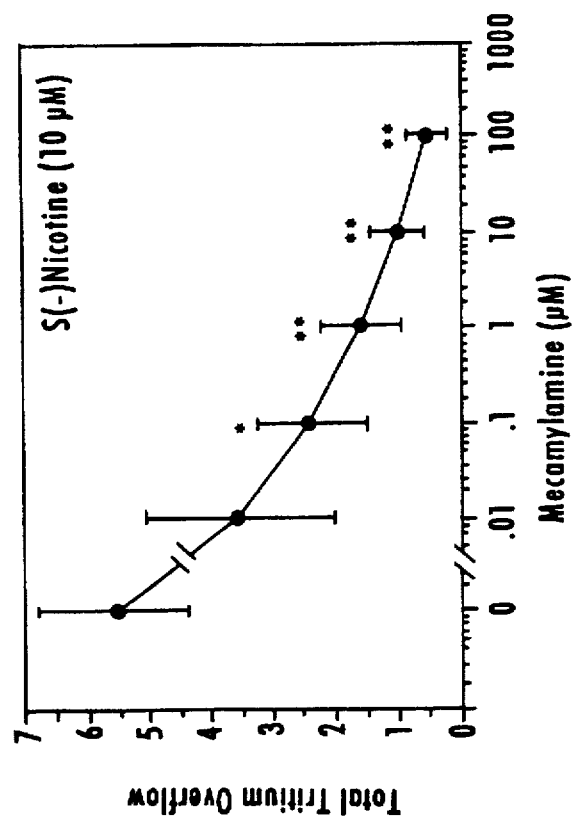
Figure 9F:
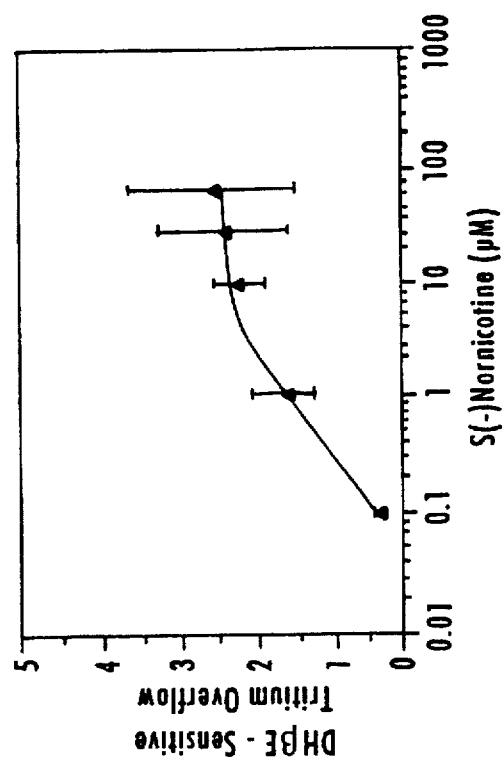
Figure 9E:
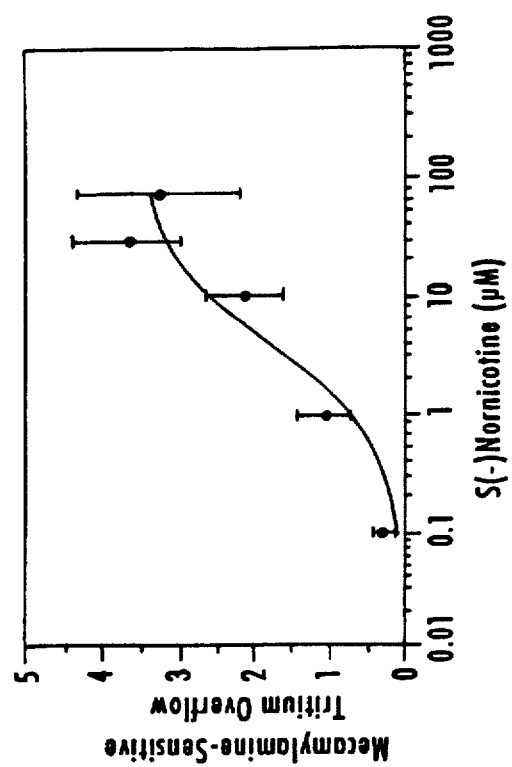

FIG. 8 shows MEC (0.01–100 µM) and DHβE (0.01–10 µM) inhibit NIC (10 tM)-evoked [$^3$H]DA release from rat striatal slices. MEC or DHβE was included in the superfusion buffer for 60 min prior to the addition of NIC, and superfusion continued for 60 min in the presence of NIC+ antagonist. Data are presented as Mean±S.E.M. total [$^3$H] overflow for N=8 rats for MEC, and N=5 for DHβE. *P<0.05, **P<0.005 different from MC-control, Fisher's LSD post hoc test.

FIG. 9 shows MEC (100 µM) or DHβE (10 µM inhibit norNIC-evoked [$^3$H]over flow from [$^3$H]preloaded rat striatal slices. Experiments were performed as described in FIG. 8. Total [$^3$H]overflow (top panel), total [$^3$H]overflow as % of norNIC-control (middle panel) and MEC-sensitive or DHβE-sensitive [$^3$H]overflow (bottom panel) are illustrated. Antagonist sensitivity was determined by subtracting the effect of norNIC in the presence of antagonist from that in it's absence for each separate experiment. *P.0.05 different from norNIC-control, Fisher's LSD post hoc test. N=5–12 rats.

Figure 10B:
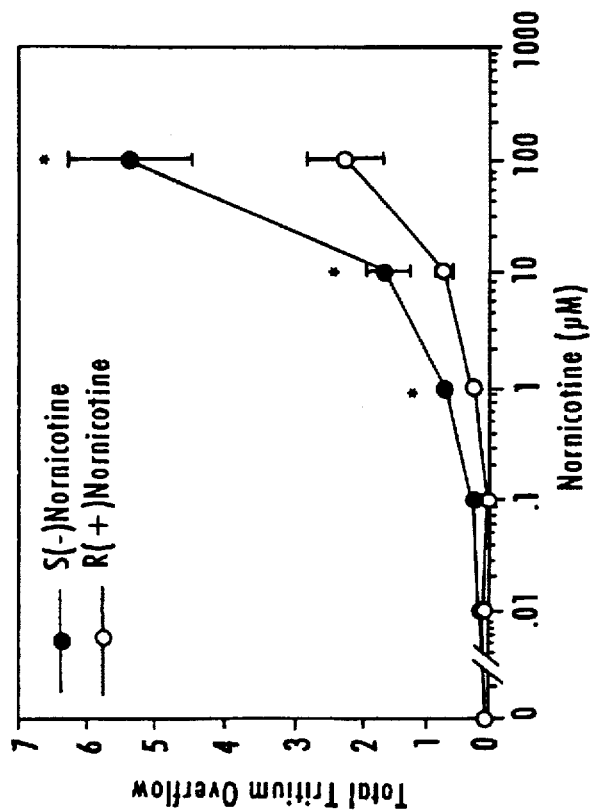
FIG. 10A and 10B show NIC and norNIC evoke a stereoselective and concentration dependent increase in [$^3$H] overflow from rat striatal slices preloaded with [$^3$H]DA. *P<0 001 different from R(+) nIC (left panel) or R(+) norNIC (right panel) N=9–14 rats.
Figure 10A:
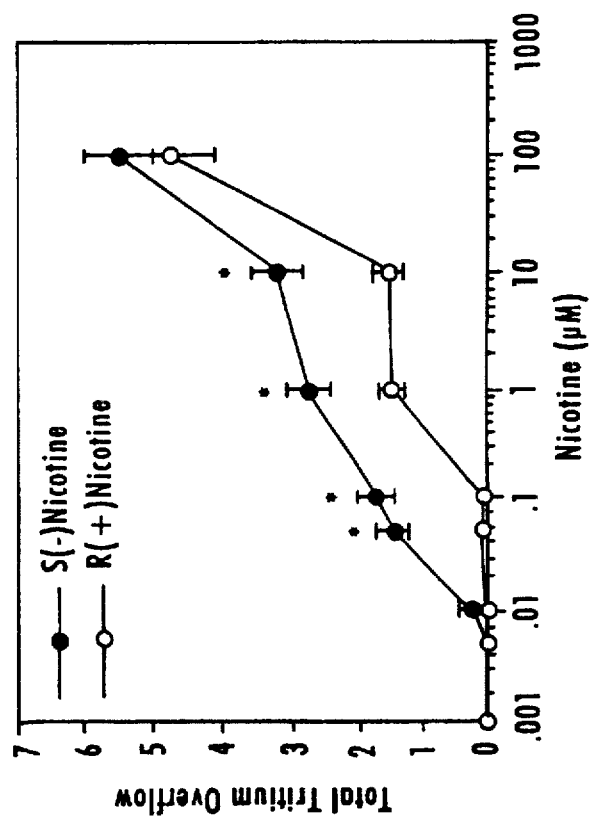

FIG. 10 shows NIC and norNIC evoke a stereoselective and concentration dependent increases in [$^3$H]overflow from rat striatal slices preloaded with [$^3$H]DA. *P<0 001 different from R(+) NIC (left panel) or R(+) norNIC (right panel) N=9–14 rats.

Figure 11:
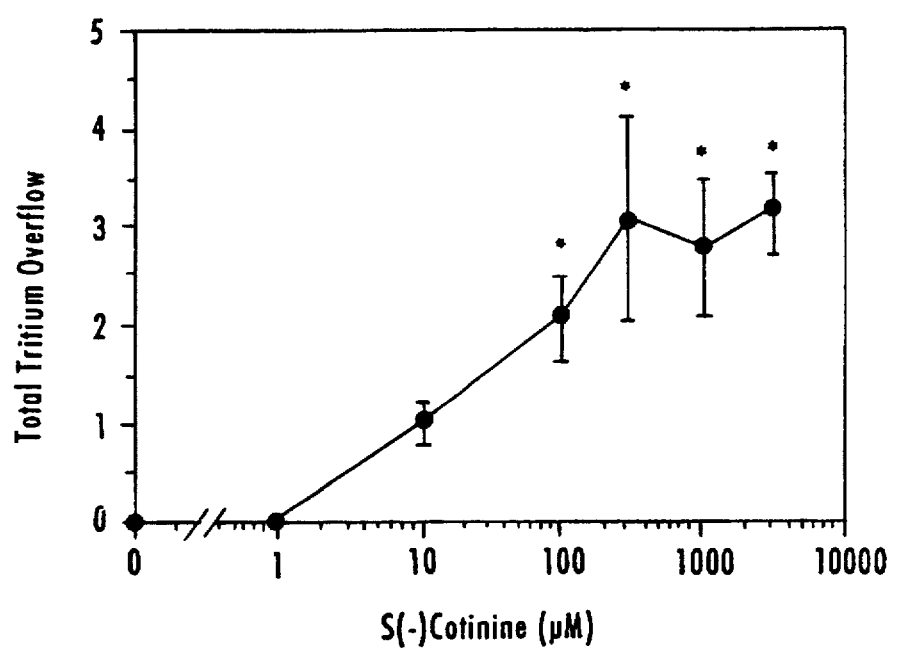
FIG. 11 shows NIC challenge induces locomotor sensitization in rats repeatedly administered R(+) norNIC, even though activity was not increased following acute or repeated R(+) norNIC administration. Locomotor activity is expressed as the cumulated number (left panel) of photobeam interruptions (Mean+SEM) during a 50 min behavioral session (right panel), which occurred immediately after each injection of drug or vehicle (saline).
Figure 12B:
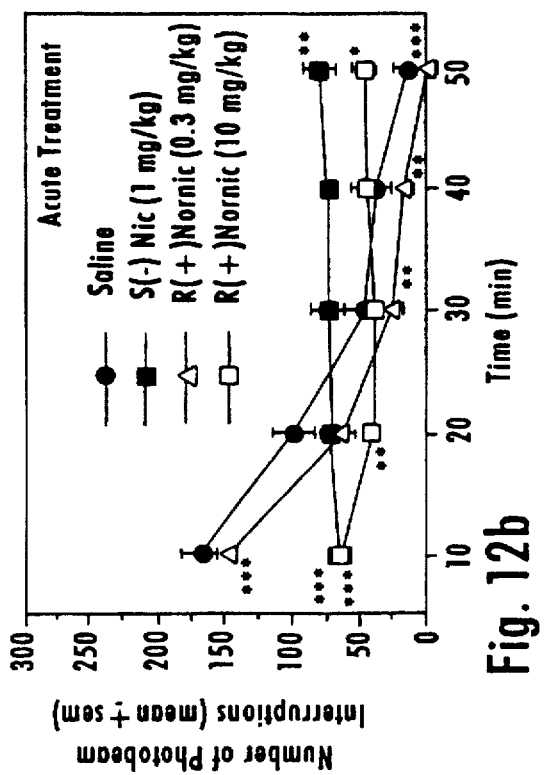
FIG. 12A and 12F show self-infusion rates for one rat responding on a continuous reinforcement schedule for amphetamine (30 µg), NIC (10µg) or NIC (50 or 100 µg).
Figure 12D:
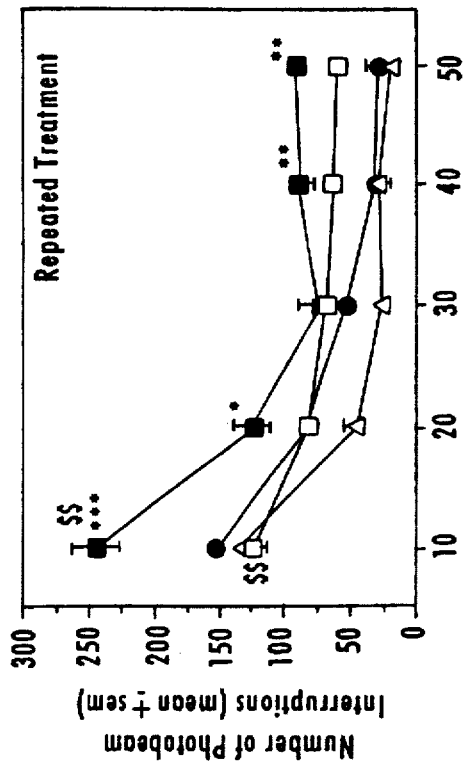
Figure 12A:
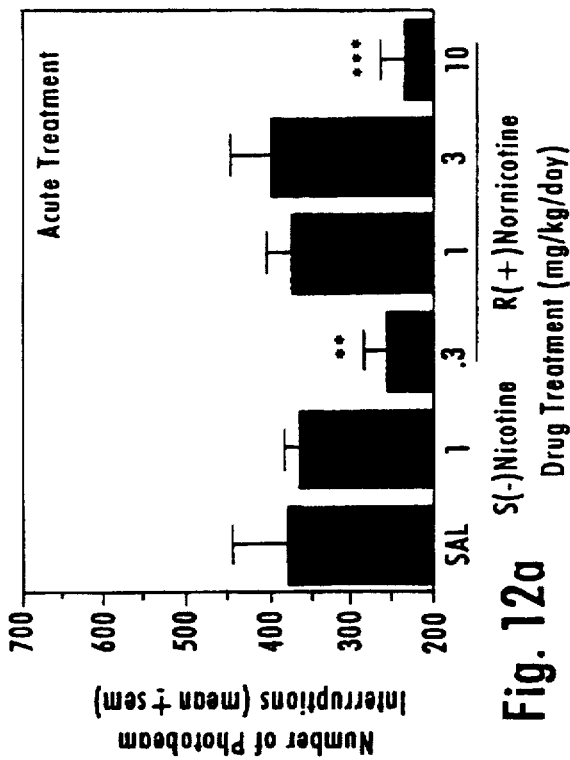
Figure 12C:
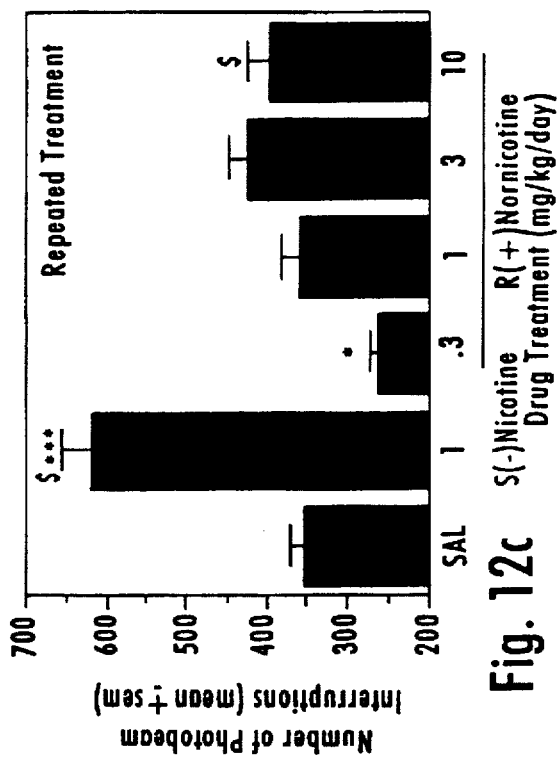
Figure 12F:
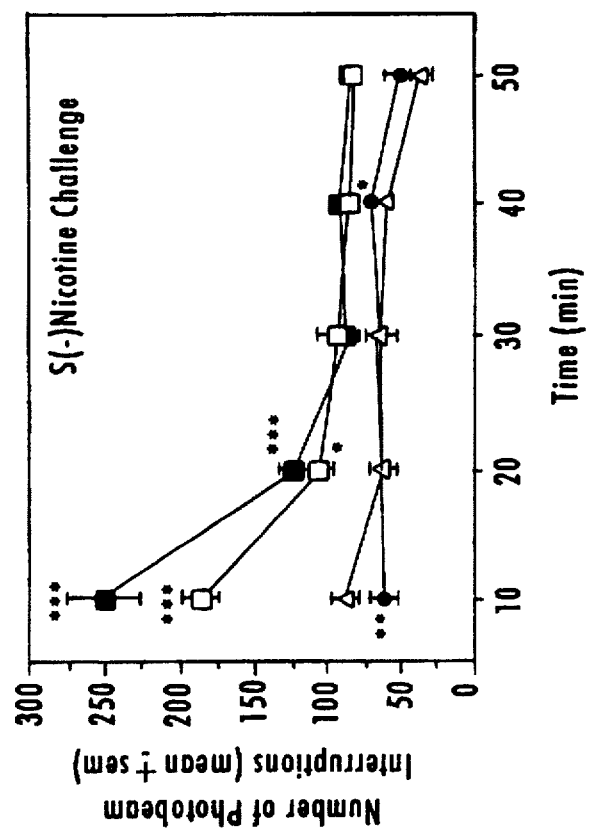
Figure 12E:
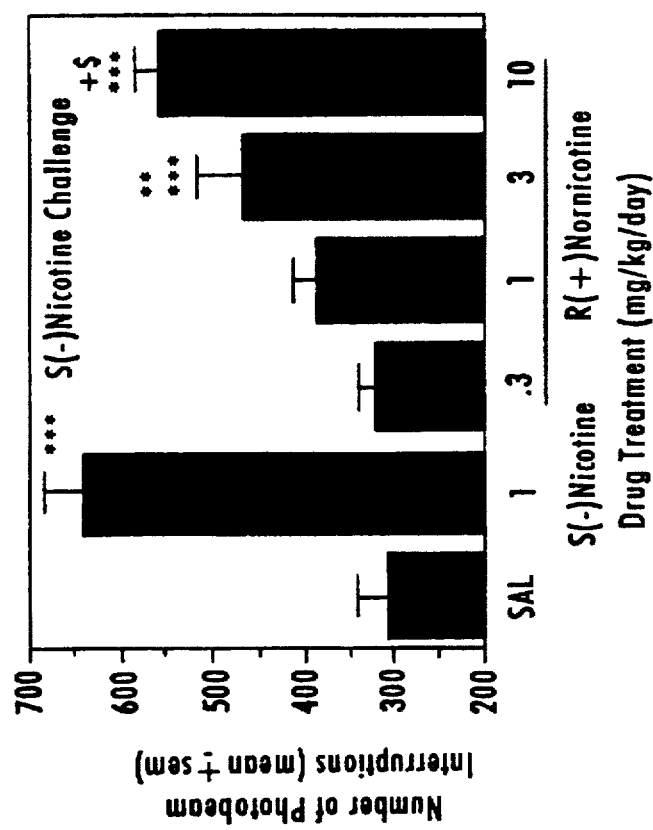

FIG. 11 shows COT evokes a concentration dependent increase in 3H overflow from rat striatal slices preloaded with 3HDA. *P, 0.05, N=6 rats.

FIG. 12. NIC challenge induces locomotor sensitization in rats repeatedly administered R(+) norNIC, even though activity was not increased following acute or repeated R(+) norNIC administration. Locomotor activity is expressed as the cumulated number (left panel) of photobeam interruptions (Mean+SEM) during a 50 min behavioral session (right panel), which occurred immediately after each injection of drug or vehicle (saline). Each bar represents a group of rats (n=6) administered a different drug treatment. Top, middle and bottom panels illustrate effects of acute, repeated (s.c., 8 injections once every 48 hrs) and MC-challenge (1 mg/kg, s.c., 48 hrs after the last dose of the repeated drug regimen for each treatment group), respectively. Treatment groups were injected with either NIC (1 mg/kg), R(+) norNIC (0.3–10 mg/kg) or saline. (For the cumulated activity: *$P<0.05$, $P<0.01$, and *$P<0.001$ compared to the saline-control group tested on the same experimental day; +$P<0.05$, ++$P<0.01$, compared to the NIC treatment group on the same experimental day, §$P<0.05$, compared to the same treatment group after acute administration, #$P<0.05$ compared to the same treatment group on the last day of the repeated administration. For the time course (right panels): *$P<0.05$, $P<0.01$, and *$P<0.001$ compared to the saline control group at the same time point on the same experimental day; +$P<0.05$, ++$P<0.01$, +++$P<0.001$ compared to the nicotine treatment group at the same time point on the same experimental day, §§$P<0.001$ compared to the same treatment group at the same time point after acute administration, #$P<0.05$, ##$P<0.001$ compared to the same treatment group at the same time point on the last day of repeated administration as determined by Duncan's New Multiple Range post hoc analysis).

FIG. 13 Self-infusion rates for one rat responding on a continuous reinforcement schedule for amphetamine (30 µg), NIC (10 µg) or NIC (50 or 100 µg).

FIG. 14. Mean percent of amphetamine-appropriate responses (top figure) and total responses (bottom figure) when amphetamine, nicotine or nornicotine were administered 15 min prior to the substitution test session.

FIG. 15. Mean percent of amphetamine-appropriate responses (top figure) and total responses (bottom figure when nicotine or nornicotine were administered 45 min prior to the substitution test session.

FIG. 16 shows time course of behavioral sessions following acute and repeated administration of S(−)nicotine or R(+)nornicotine and the effect of subsequent challenge with S(−)nicotine. Locomotor activity is expressed as the number of photobeam interruptions (Mean±SEM) as a function of time (min) during a 50 min behavioral session, which occurred immediately after each injection of drug or vehicle (saline). Top panel illustrates the effects of acute administration (s.c.) of S(−)nicotine (1 mg/kg), R(+)nornicotine (0.3 and 10 mg/kg) or saline. Middle panel illustrates the effect of repeated administration (s.c., 8 injections once every 48 hr) of S(−)nicotine (1 mg/kg), R(+)nornicotine (0.3 and 10 mg/kg), or saline; and, locomotor activity measured immediately following the eighth (last) injection. Bottom panel illustrates the effect of challenge 27 with S(−)nicotine (1 mg/kg, s.c.) 48 hrs after the last dose of the repeated drug administration for each treatment group. (*$P<0.05$, $P<0.01$, and *$P<0.001$ compared to the saline-control group at the same time point on the same experimental day; +$P<0.05$, ++$P<0.01$, +++$P<0.001$ compared to the nicotine treatment group at the same time point on the same experimental day; § §$P<0.001$ compared to the same treatment group at the same time point after acute administration; #$P<0.05$, ##$P<0.001$ compared to the same treatment group at the same time point on the last day of repeated administration; as determined by Duncan's New Multiple Range post hoc analysis).

FIG. 17 shows behavioral sensitization and cross-sensitization following repeated administration of S(−) nicotine or S(−) nornicotine. Locomotor activity is expressed as the cumulated number of photobeam interruptions (Mean±SEM) during a 50 min behavioral session, which occurred immediately after each injection of drug or vehicle (saline). Each bar represents a group of rats (n=6) administered a different drug treatment. The treatment groups were tested repeatedly in the behavioral apparatus and the results are illustrated in the different panels. Top panel illustrates the effects of acute administration (s.c.) of S(−) nicotine (1 mg/kg), S(−) nornicotine (0.3–10 mg/kg) or saline. Middle panel illustrates the effect of repeated administration (s.c., once every 48 furs) of S(−) nicotine (1 mg/kg), S(−) nornicotine (0.3–10 mg/kg), or saline; and, locomotor activity measured immediately following the eighth (last) injection. Bottom panel illustrates the effect of challenge with S(−) nicotine (1 mg/kg, s.c.) 48 hrs after the last dose of the repeated drug administration for each treatment group. (*$P<0.05$, $P<0.01$, and *$P<0.001$ compared to the saline control group tested on the same experimental day; $P<0.05$, §§$P<0.001$ compared to the same treatment group after acute administration; as determined by Duncan's New Multiple Range post hoc analysis).

FIG. 18 shows time course of behavioral sessions following acute and repeated administration of S(−) nicotine or S(−) nornicotine and the effect of subsequent challenge with S(−) nicotine. Locomotor activity is expressed as the number of photobeam interruptions (Mean±SEM) as a function of time (min) during a 50 min behavioral session, which occurred immediately after each injection of drug or vehicle (saline).

REFERENCES

1. Bowman, E. R.; Turnbull, L. B.; McKennis H. T\Metabolism of nicotine in the human and excretion of pyridine compounds by smokers. J. Pharmacol. Exp. Ther. 127:91–102; 1959.
2. Callahan, P. M.; Appel, J. B.; Cunningham, K. A. Dopamine $D_1$ and $D_2$ mediation of the discriminative stimulus properties of d-amphetamine and cocaine. Psychopharmacology 103:50–55; 1991.
3. Carboni, E.; Acquas, E.; Leone, P.; Di Chiara, G. $5HT_3$ receptor antagonists block morphine- and nicotine- but not amphetamine-induced reward. Psychopharmacology 97:175–178; 1989.
4. Change, W. T.; Murfin, D.; Krynock, G. M. Rosecrans, J. A. A description of the nicotine stimulus and tests of its generalization to amphetamine. Psychopharmacology 55:19–26; 1977.
5. Crooks, P. A.; Li, M.; Dwoskin, L. P. Determination of nicotine metabolites in rat brain after peripheral radiolabled nicotine administration: Detection of nornicotine. Drug Metab. Dispos. 23:1175–1177; 1995.
6. Di Chiara, G.; Imperato, A. Drugs abused by humans preferentially increase synaptic dopamine concentrations in the mesolimbic system of freely moving rats. Proc. Natl. Acad. Sci. USA 85:5274–5278; 1988.
7. Dwoskin, L. P.; Crooks, P. A.; Marion, M. B.; Teng, L. H.; Bardo, M. T. Nornicotine, the minor tobacco alkaloid and active nicotine metabolite, enables behavioral sensitization to nicotine in rats. Manuscript submitted.
8. Evans, S. M.; Johanson C. E. Discriminative stimulus properties of histamine $H_1$-antagonists in animals trained to discriminate d-amphetamine or pentobarbital. J. Pharamcol. Exp. Ther. 250:779–787; 1989.
9. Fowler, S. C.; Johnson, J. S.; Kallman, M. J.; Liou, J. R.; Wilson, M. C.; Hikal, A. H. In a drug discrimination procedure isolation-reared rats generalize to lower doses of cocaine and amphetamine than rats reared in an enriched environment. Psychopharmacology 110:115–118; 1993.
10. Hirschhorn, I. D.; Rosecrans, J. A. Studies on the time course and the effect of cholinergic and adrenergic receptor blockers on the stimulus effect of nicotine. Psychopharmacologia 40:109–120; 1974.
11. Ho, B. T.; Huang, J. T. Role of dopamine in d-amphetamine-induced discriminative responding. Pharamcol. Biochem. Behav. 3:1085–1092; 1975.
12. Iwamoto, E. T. Nicotine conditions place preferences after intracerebral administration in rats. Psychopharmacology 100:251–257; 19909.
13. Leikola-Pelho and Jackson, 1992
14. Nisell, M.; Nomikos, G. G.; Svensson, T. H. Systemic nicotine-induced dopamine release in the rat nucleus accumbens is regulated by nicotinic receptors in the ventral tegmental area. Synapse 16:36–44; 1994.
15. Reavill, C.; Stolerman, I. P. Interaction of nicotine with dopaminergic mechanisms assessed through drug discrimination and rotational behavior in rats. J. Pharamcol. 1:264–273; 1987.
16. Reavill and Stolerman, 1990
17. Risner, M. E.; Cone, E. J.; Benowitz, N. L.; Jacob, P. J. Effects of stereoisomers of nicotine and nornicotine on schedule controlled responding and physiological parameters of dogs. J. Pharamcol. Exp. Ther. 244:807–813; 1988.
18. Risner, M.E.; Goldberg, S. R.; Prada, J. A.; Cone, E. J. Effects of nicotine, cocaine and some of their metabolites on schedule controlled responding by beagle dogs and squirrel monkeys. J. Pharmacol. Exp. Ther. 234:113–119; 1985.
19. Schechter, M.; Meehan, S. M. Dopaminergic mediation of the stimulant generalization of nicotine, Prog. Neuro-Psychopharmacol. Bio. Psychiat. 17:835–845; 1993.
20. Singer, G.; Wallace, M.; Hall, R. Effects of dopaminergic nucleus accumbens lesions on the acquisition of schedule-induced self-injection of nicotine in the rat. Pharmacol. Biochem. Behav. 17:579–581; 1982.
21. Stolerman, I. P.; Pratt, J. A.; Garcha, H. S.; Giardini, V.; Kumar, R. Nicotine cue in rats analyzed with drugs acting on cholinergic and 5-hydroxytryptamine mechanisms. Neuropharmacology 22:1029–1037; 1983.
22. West, W. B.; Van Groll, B. J.; Appel, J. B. Stimulus effects of d-amphetamine II: DA, NE, and 5-HT mechanisms. Pharmacol. Biochem. Behav. 51:69–76; 1995.
23. Whiteaker, et al. 1995
24. Zhang, Y.; Jacob, P.; and Benowitz, N. D. Determination of nornicotine in smokers' urine by gas chromatography following reductive alkylation to N'-propylnornicotine. J. Chromatog. 525-349–357; 1990.
25. Alkondon M and Albuquerque EX. (1991) Initial characterization of the nicotinic acetylcholine receptorsin rat hippocampal neurons. J Recept Res 11:1001–1021.
26. Balfour DJK and Benwell MEM (1993) The role of brain dopamine systems in the psychopharmacological responses to nicotine. Asia Pacific Journal of Pharmacol 8:153–167.
27. Clarke PBS (1987) Nicotine and smoking: A perspective from animal studies. Psychopharmacol 92:135143.
28. Clarke PBS and Pert A (1985) Autoradiographic evidence for nicotine receptors on nigrostriatal and mesolimbic dopaminergic neurons. Brain Res 348:355–385.
29. Crooks P. A., Li M, Porter T. D. and Dwoskin L. P. (1996) Metabolites of nicotine in rat brain after peripheral nicotine administration: Cotinine, nornicotine and norcotinine. Drug Metab Disposit submitted.
30. Crooks P. A., Ravard A, Wilkins L. H., Teng L. H., Buxton S. T. and Dwoskin L. P. (1995) Inhibition of nicotine-evoked [3H]dopamine release by pyridino N-substituted nicotine analogues: A new class of nicotinic antagonist. Drug Development Res, 36:91–102.
31. Damaj Ml, Welch S. P. and Martin B. R. (1995) In vivo pharmacological effects of dihydro-erythroidine, a nicotinic antagonist, in mice. Psychopharmacol 117:67–73.
32. Dwoskin L. P., Buxton S. T., Jewell A. L. and Crooks P. A. (1993) S(–) nornicotine increases dopamine release in a calcium-dependent manner from superfused rat striatal slices. J Neurochem 60:2167–2174.
33. Fibiger H. C. and Phillips A. G. (1987) Role of catecholamine transmitters in brain reward systems: Implications for the neurobiology of affect. In: Engel J., Oreland L. (eds) Brain Reward Systems and Abuse, Raven Press, New York, pp 61–74.
34. Grady S. R., Marks M. J. and Collins A. C. (1994) Desensitization of nicotine-stimulated [3H] DA release from mouse striatal synaptosomes.
35. Loiacono R, Stephenson J, Stevenson J and Mitchelson F (1993) Multiple binding sites for nicotine receptor antagonists in inhibiting [3H] (–)-nicotine binding in rat cortex. Neuropharmacol 32:847–853.
36. Martin T. J., Suchocki J, May E. L. and Martin B. R. (1990) Pharmacological evaluation of the antagonism of nicotine's central effects by mecamylamine and pempidine. J Pharmacol Exp Ther 254:45–51.
37. Mulle C., Vidal C., Benoit P. and Changeux J. P. (1991) Existence of different subtypes of nicotinic acetylcholine receptors in the rat habenulo-interpeduncular system. J Neurosci 11:2588–2597.
38. Peng O. , Gerzanich V., Anand R., Whiting P. J. and Lindstrom J. (1994) Nicotine-induced increase in the neuronal nicotinic receptors results from a decrease in the rate of receptor turnover. Mol Pharmacol 46:523–530.
39. Risner M. E., Cone E. J., Benowitz N. L. and Jacob P. J. (1988) Effects of stereoisomers of nicotine and nornicotine on schedule controlled responding and physiological parameters of dogs. Pharmacol Exp Ther 244:807–813.
40. Rose J. E., Behm F. M., Westman E. C., Levin E. D., Stein R. M., Lane J. D. and Ripka G. V. (1994) Combined effects of nicotine and mecamylamine in attenuating smoking satisfaction. Exp and Clin Psychopharmacol 2:328–344.
41. Shoaib M., Stolerman I. P. and Kumar R. C. (1994) Nicotine-induced place preferences following prior nicotine exposure in rats. Psychopharmacol 113:445–452.
42. Singer G., Wallace M. and Hall R. (1982) Effects of dopaminergic nucleus accumbens lesions on the acquisition of schedule-induced self-injection of nicotine in the rat. Pharmacol Biochem Behav 17:579–581
43. Teng L. H., Buxton S. T., Crooks P. A. and Dwoskin L. P. (1996) Evidence for nicotinic-receptor mediation of nornicotine-evoked [3H] overflow from rat striatal slices preloaded with [3H] dopamine:

Comparison with S(–) nicotine. J Neurochem submitted.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A method of treating dopamine mediated disease states comprising administering to an individual in need of such treatment an effective amount of a composition comprising a compound selected from the group consisting of S-(–) nornicotine or R-(+) nornicotine, free base forms, inorganic acid salts and organic acid salt forms thereof, said composition being administered outside the central nervous system and in an amount effective to cross the blood-brain barrier.

2. The method of claim 1 wherein said dopamine mediated disease state is selected from the group consisting of myasthenia gravis, Parkinson's disease, Alzheimer's disease, schizophrenia, eating disorders, and drug addiction, or wherein the composition is used as a substitute for psycho-stimulant self-administration.

3. The method of claim 2 wherein said drug addiction is to a drug selected from the group consisting of nicotinic agonists, cocaine, amphetamines, caffeine, phencyclidine, opiates, barbituates, benzodiazepines, cannabinoids, hallucinogens and alcohol.

4. The method of claim 1 wherein said composition further comprises a pharmaceutical carrier.

5. The method of claim 4, wherein said composition is a pharmaceutical formulation for a form of delivery selected from the group consisting of oral, transdermal, transnasal, rectal, sublinguinal, subdermal, intraocular and inhalation smokeless delivery.

6. A method of displacement of nicotine from nicotinic receptor sites in the brain comprising administering to an individual in need of such treatment an effective amount of S-(−)-Nornicotine or R-(+)-Nornicotine to cause displacement of nicotine from nicotinic receptor sites in the brain, said nornicotine being administered outside the central nervous system and in an amount sufficient to cross the blood-brain barrier.

7. A method of obtaining release from presynaptic terminals in neuronal dopamine tissue in a stereoselective and receptor-mediated manner comprising administering to an individual in need of such treatment an effective amount of S-(−)-Nornicotine or R-(+)-Nornicotine to obtain dopamine release, said nornicotine being administered outside the central nervous system and in an amount sufficient to cross the blood-brain barrier.

8. A method of activating the mechanism involved in behavioral sensitization to psycho-stimulants which is correlated with craving in humans comprising administration to an individual in need of such treatment of S-(−)- or R-(+)-nornicotine, said nornicotine being administered outside the central nervous system and in an amount sufficient to cross the blood-brain barrier.

9. The method of claim 1, wherein said free base forms of S-(−) nornicotine or R-(+) nornicotine are selected from the group consisting of.

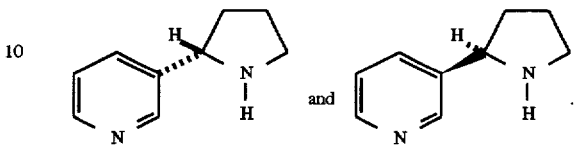

10. The method of claim 1, wherein said acid salts of S-(−) nornicotine or R-(+) nornicotine are selected from the group consisting of hydrochloride, hydrobromide, perchlorate, ascorbate, sulfate, tartrate, fumarate, citrate, malate, lactate, aspartate, mesylate, benzenesulfonate, proprionate and mixtures thereof.

11. The method of claim 1 wherein the step of administering an effective amount comprises administering from about 0.2 to about 35 mg per kg of body weight of said composition between one and three times daily.

12. The method of claim 11 wherein the step of administering includes administering said composition orally.

13. The method of claim 11 wherein the step of administering includes administering said composition rectally.

14. The method of claim 1 wherein the step of administering an effective amount comprises administering from about 10 to about 60 mg of said composition once or twice daily.

15. The method of claim 14 wherein the step of administering includes administering said composition intramuscularly.

16. The method of claim 14 wherein the step of administering includes administering said composition transdermally.

* * * * *